US012668776B2

(12) United States Patent
    Davila

(10) Patent No.: US 12,668,776 B2
(45) Date of Patent: Jun. 30, 2026

(54) ARTIFICIAL ANTIGEN PRESENTING CELLS COMPRISING PROTEIN L FOR EXPANDING IMMUNE CELLS FOR IMMUNOTHERAPY

(71) Applicant: H. LEE MOFFITT CANCER CENTER AND RESEARCH INSTITUTE, INC., Tampa, FL (US)

(72) Inventor: Marco Davila, Tampa, FL (US)

(73) Assignee: H.LEE MOFFITT CANCER CENTER AND RESEARCH INSTITUTE, INC., Tampa, FL (US)

(*) Notice: Subject to any disclaimer, the term of this patent is extended or adjusted under 35 U.S.C. 154(b) by 710 days.

(21) Appl. No.: 16/972,202

(22) PCT Filed: Jun. 5, 2019

(86) PCT No.: PCT/US2019/035486
    § 371 (c)(1),
    (2) Date: Dec. 4, 2020

(87) PCT Pub. No.: WO2019/236647
    PCT Pub. Date: Dec. 12, 2019

(65) Prior Publication Data
    US 2021/0230543 A1      Jul. 29, 2021

Related U.S. Application Data

(60) Provisional application No. 62/680,951, filed on Jun. 5, 2018.

(51) Int. Cl.
    *C12N 5/0783*     (2010.01)
    *A61K 35/17*      (2015.01)
    *A61K 40/11*      (2025.01)
    *A61K 40/15*      (2025.01)
    *A61K 40/31*      (2025.01)
    *A61K 40/45*      (2025.01)

(52) U.S. Cl.
    CPC ............ *C12N 5/0636* (2013.01); *A61K 35/17* (2013.01); *A61K 40/11* (2025.01); *A61K 40/15* (2025.01); *A61K 40/31* (2025.01); *A61K 40/45* (2025.01); *C12N 5/0638* (2013.01); *C12N 2502/1114* (2013.01)

(58) Field of Classification Search
    CPC .......... C12N 5/0636; C12N 2502/1114; C12N 2502/30; C12N 2502/99; C12N 2510/00; C12N 5/0638; A61K 39/4611; A61K 39/4613; A61K 39/4631; A61K 39/4648; A61K 35/17; A61K 39/02; A61P 35/00; C07K 14/195
    See application file for complete search history.

(56) References Cited

U.S. PATENT DOCUMENTS

| | | | | |
|---|---|---|---|---|
| 7,745,140 | B2 * | 6/2010 | June ................ | C07K 14/70535 |
| | | | | 435/7.1 |
| 2007/0275873 | A1 | 11/2007 | Heidner et al. | |
| 2010/0028450 | A1 | 2/2010 | Vasu | |
| 2018/0002397 | A1 | 1/2018 | Shah et al. | |

FOREIGN PATENT DOCUMENTS

| | | | | |
|---|---|---|---|---|
| WO | 2018053463 | A1 | 3/2018 | |
| WO | 2018081784 | A1 | 5/2018 | |
| WO | WO-2018102795 | A2 * | 6/2018 | ................ A61P 3/10 |

OTHER PUBLICATIONS

Ye, Q., Loisiou, M., Levine, B.L. et al. Engineered artificial antigen presenting cells facilitate direct and efficient expansion of tumor infiltrating lymphocytes. J Transl Med 9, 131 (2011). https://doi.org/10.1186/1479-5876-9-131 (Year: 2011).*
International Search Report and Written Opinion in PCT/US2019/035486. Mailed Aug. 16, 2019. 8 pages.
Cheung, AS et al. Scaffolds that mimic antigen-presenting cells enable ex vivo expansion of primary T cells. Nature Biotechnology. Feb. 2018.
Extended European Search Report issued for U.S. Appl. No. 19/815,714, dated Mar. 18, 2022.
Zheng, Zhili, Nachimuthu Chinnasamy, and Richard A. Morgan. "Protein L: a novel reagent for the detection of chimeric antigen receptor (CAR) expression by flow cytometry." Journal of translational medicine 10.1 (2012):29. 6 pages.
Xiao, Lin, et al. "Large-scale expansion of Vγ9Vδ2 T cells with engineered K562 feeder cells in G-Rex vessels and their use as chimeric antigen receptor-modified effector cells." Cytotherapy 20.3 (2018): 420-435.
Rushworth, David, et al. "Universal artificial antigen presenting cells to selectively propagate T cells expressing chimeric antigen receptor independent of specificity." Journal of immunotherapy (Hagerstown, Md.: 1997) 37.4 (2014): 204-213.
Walker, Alec J., et al. "Tumor antigen and receptor densities regulate efficacy of a chimeric antigen receptor targeting anaplastic lymphoma kinase." Molecular Therapy 25.9 (2017): 2189-2201.

(Continued)

*Primary Examiner* — Jeremy C Flinders
*Assistant Examiner* — Masudur Rahman
(74) *Attorney, Agent, or Firm* — Meunier Carlin & Curfman LLC

(57) ABSTRACT

Disclosed herein are methods of expanding immune cells for immunotherapy and/or increasing the purity of a population of CAR T cells using artificial antigen presenting cells (aAPCs) having on their surface Protein L. The disclosed aAPCs can also secrete antibodies that bind molecules of the T cell inhibitory pathway. For example, anti-CD3 scFv on the surface of the aAPCs can bind and activate T cells, while anti-CD28 scFv and 4-1BBL on the surface of the aAPCs can provide dual co-stimulation for the T cells resulting in decreased levels of the markers CD25, TIM3, LAG3, and PD1. For example, blocking PD1/PDL1 ligation can limit suppression that is mediated by the tumor microenvironment. This is a less costly and more efficient alternative to peripheral blood mononuclear cells (PBMCs) and cytokine treatments that result in better quality T cell for adoptive transfer back into patients.

14 Claims, 28 Drawing Sheets

(56) References Cited

OTHER PUBLICATIONS

International Preliminary Report on Patentability dated Dec. 17, 2020.

Fournié, J.J. et al. What lessons can be learned from γδ T cell-based cancer immunotherapy trials? Cell Mol Immunol. 10(1):35-41(Jan. 2013).

Kobayashi, H. & Tanaka, Y. γδ T Cell Immunotherapy—A Review. Pharmaceuticals (Basel). 8(1):40-61(Feb. 12, 2015).

* cited by examiner

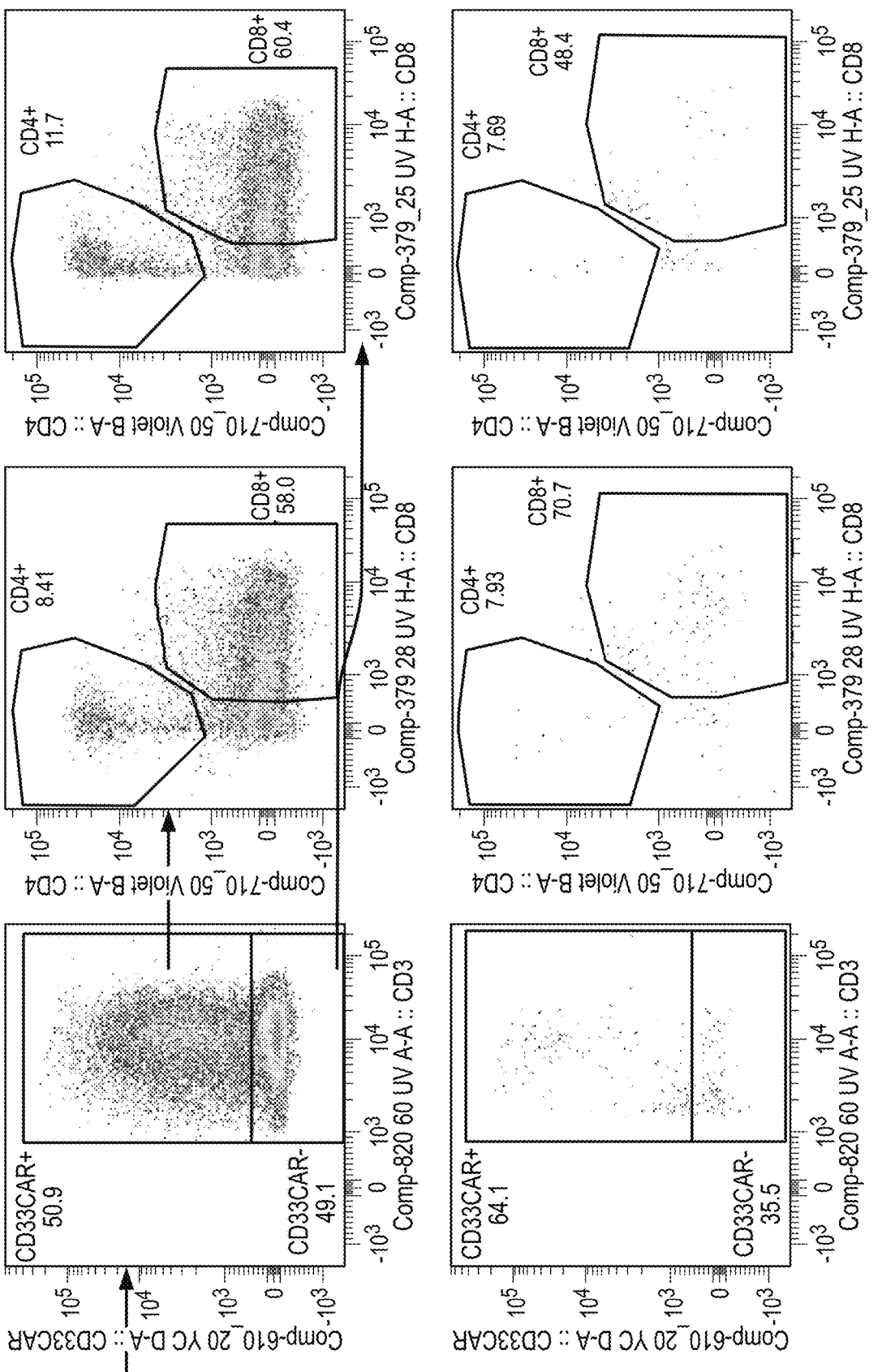
FIG. 4A (Cont. 1)

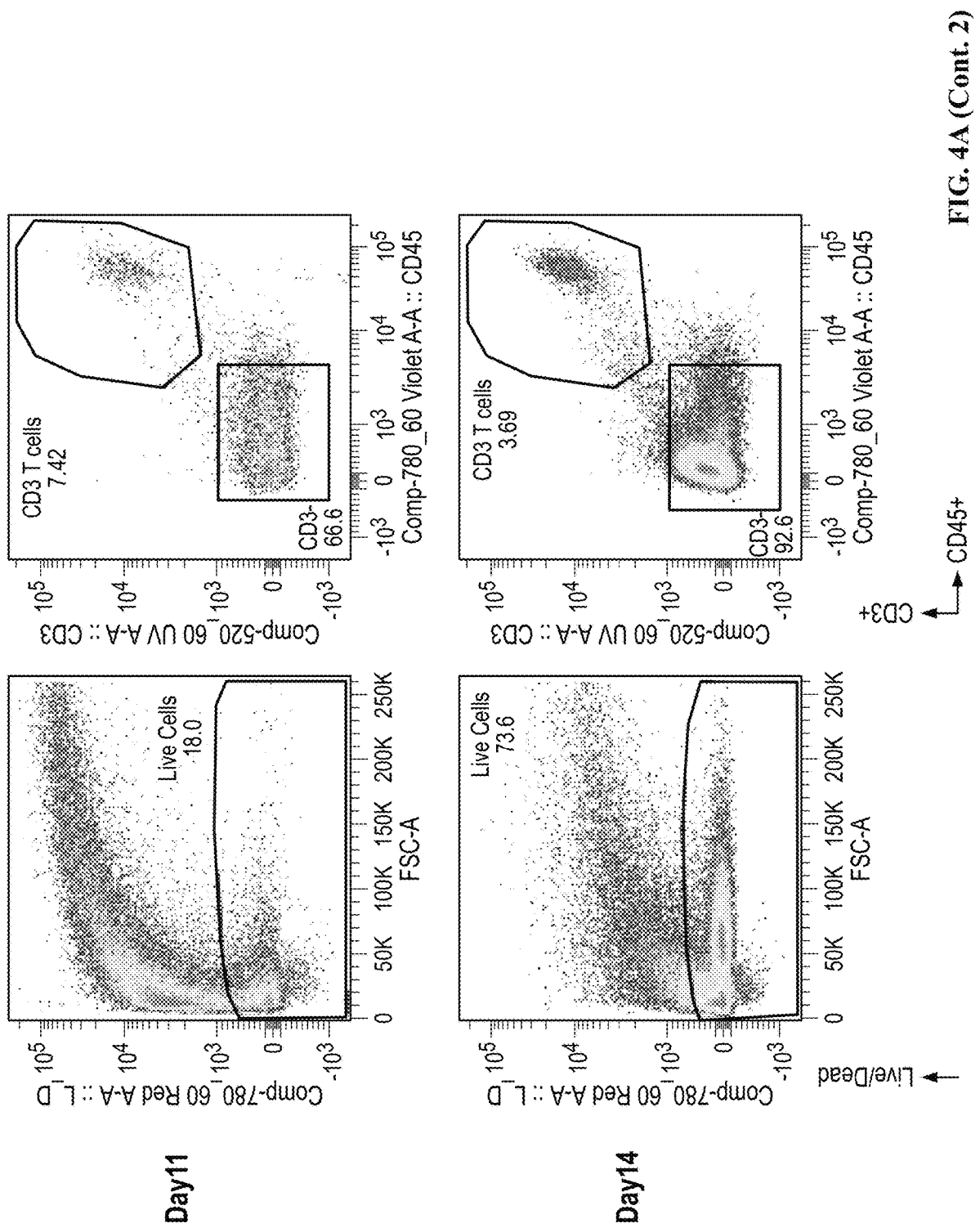
FIG. 4A (Cont. 2)

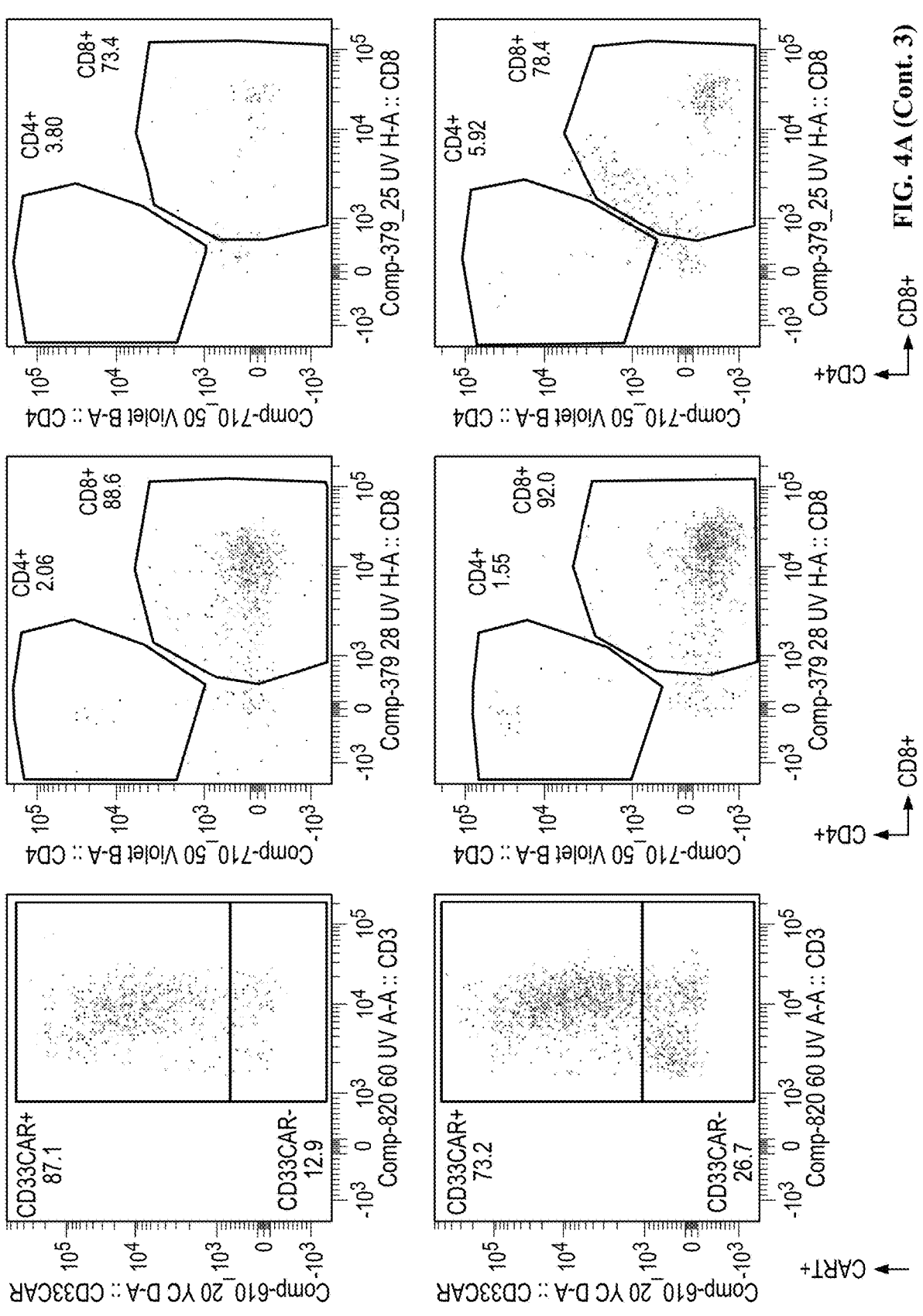
FIG. 4A (Cont. 3)

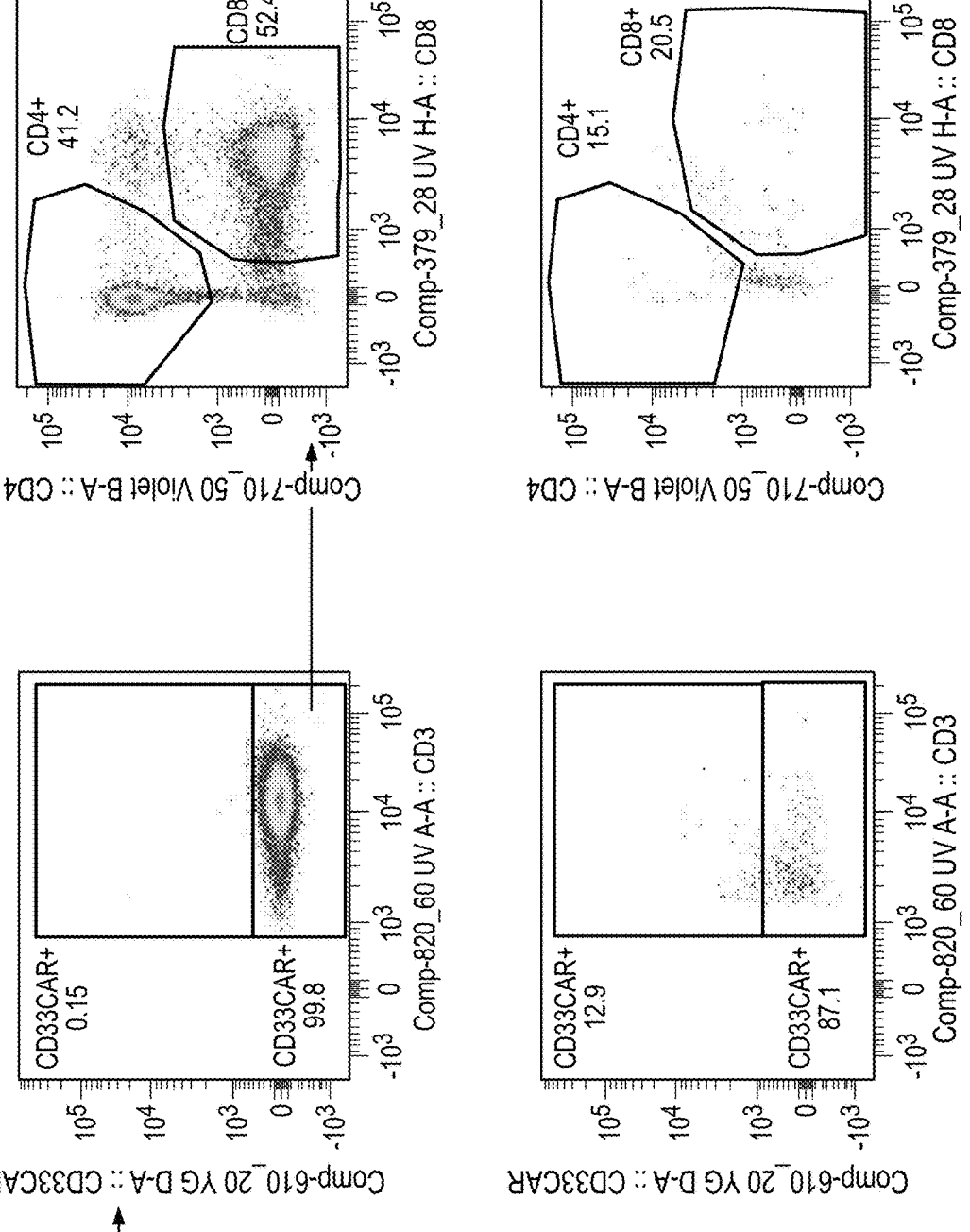
FIG. 4B (Cont. 1)

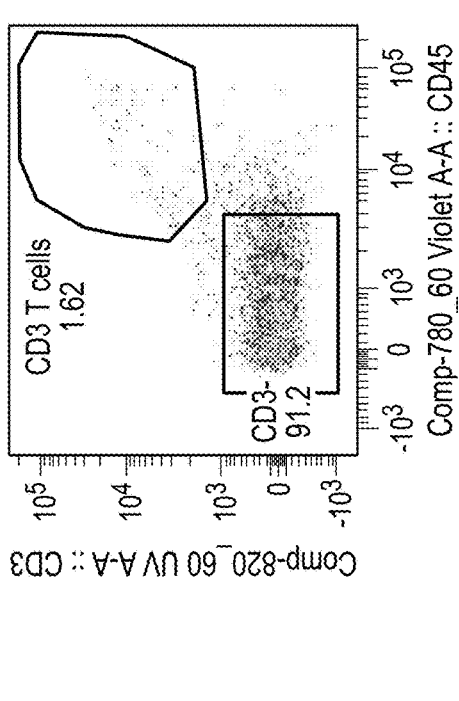
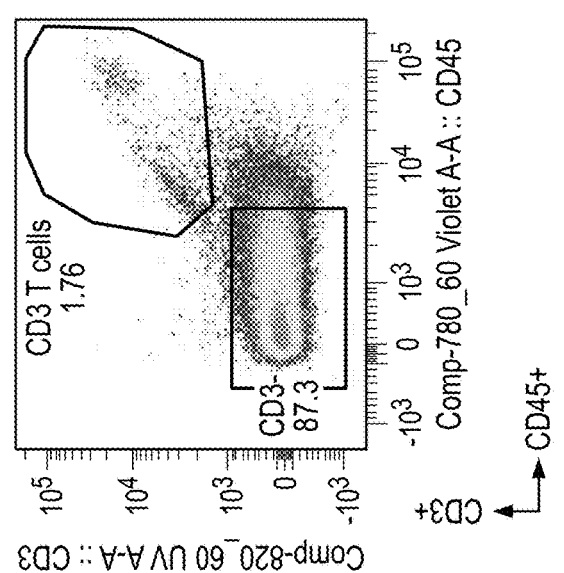
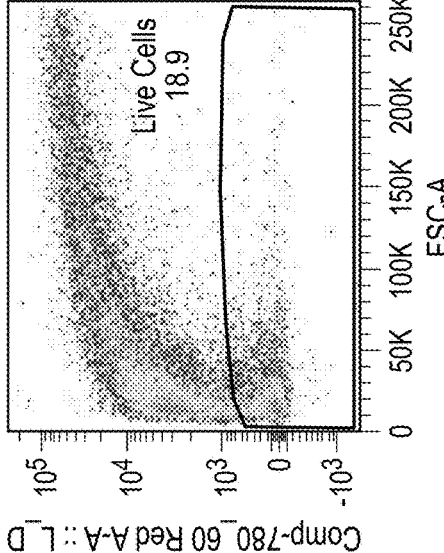
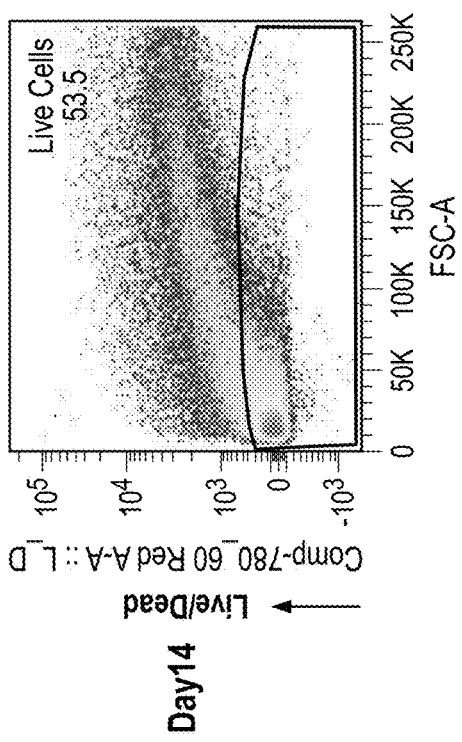
FIG. 4B (Cont. 2)

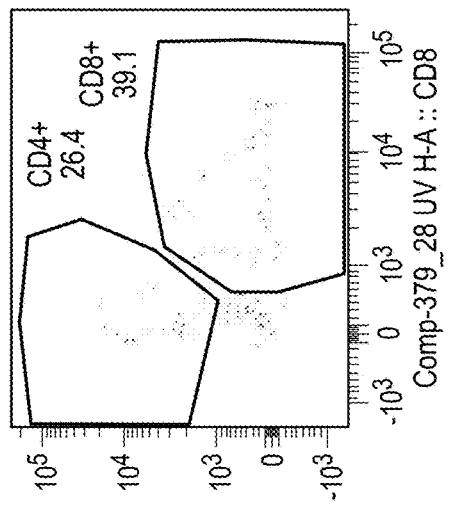
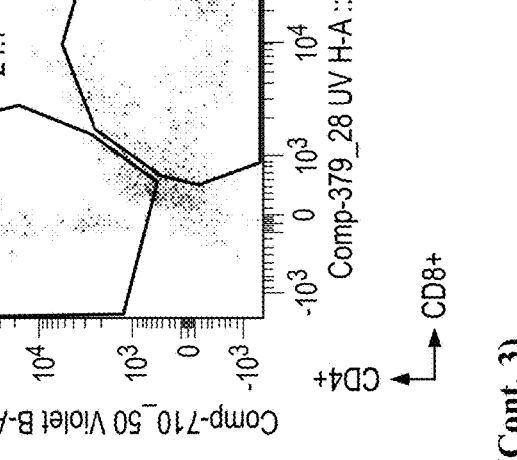
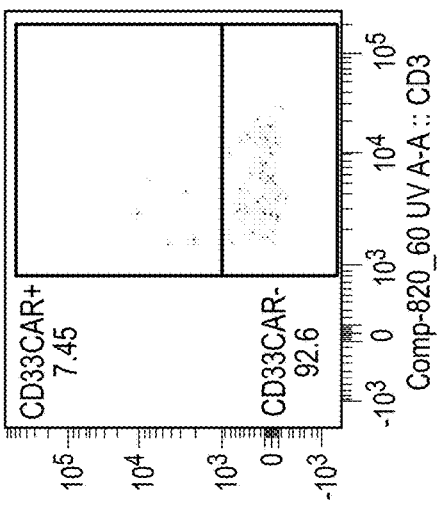
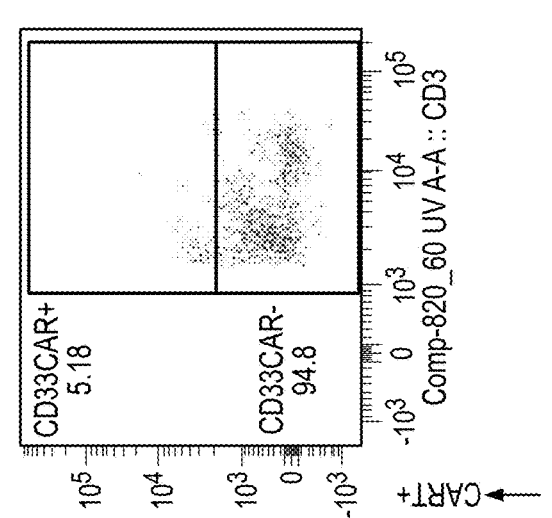
FIG. 4B (Cont. 3)

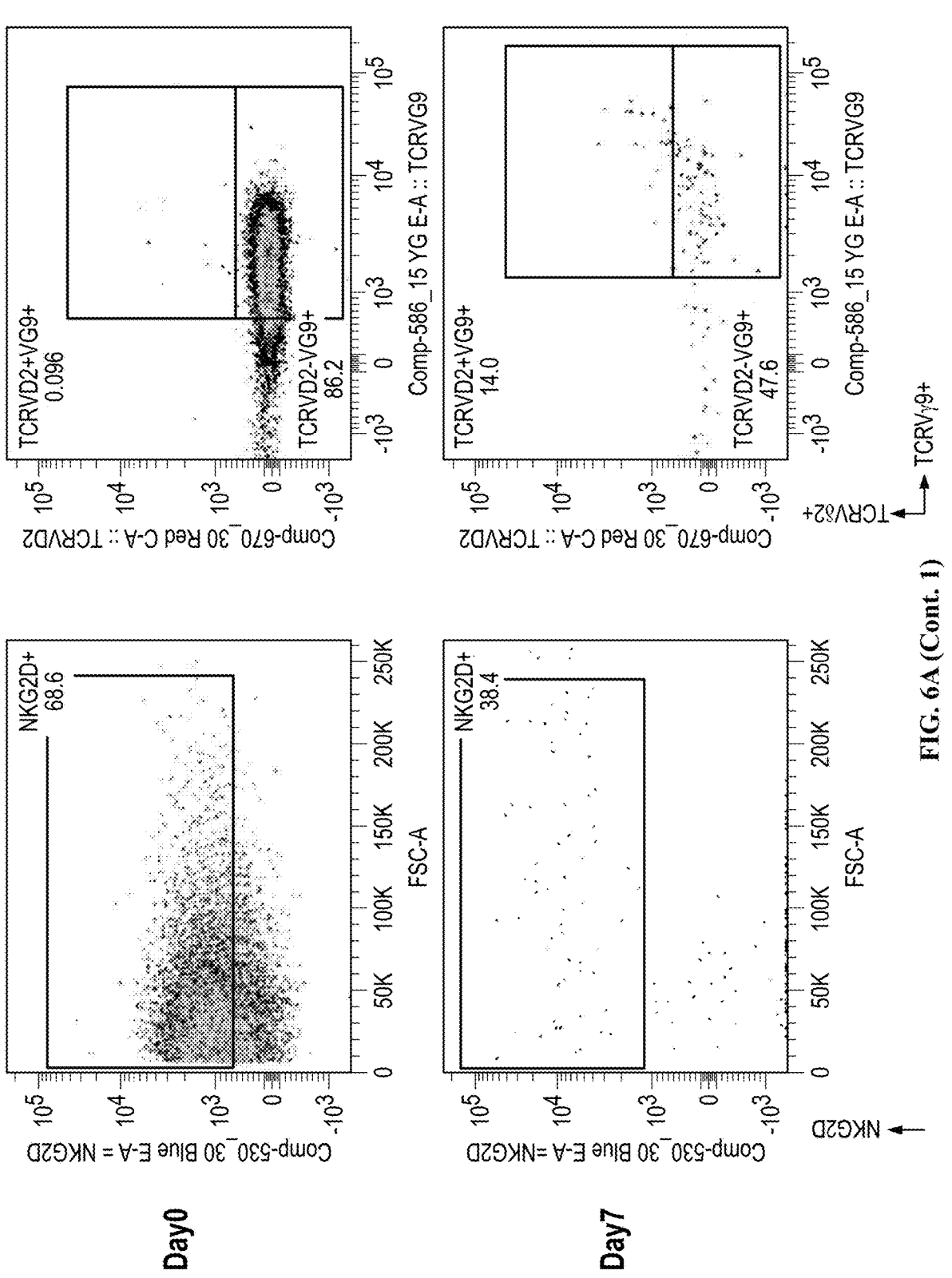
FIG. 6A (Cont. 1)

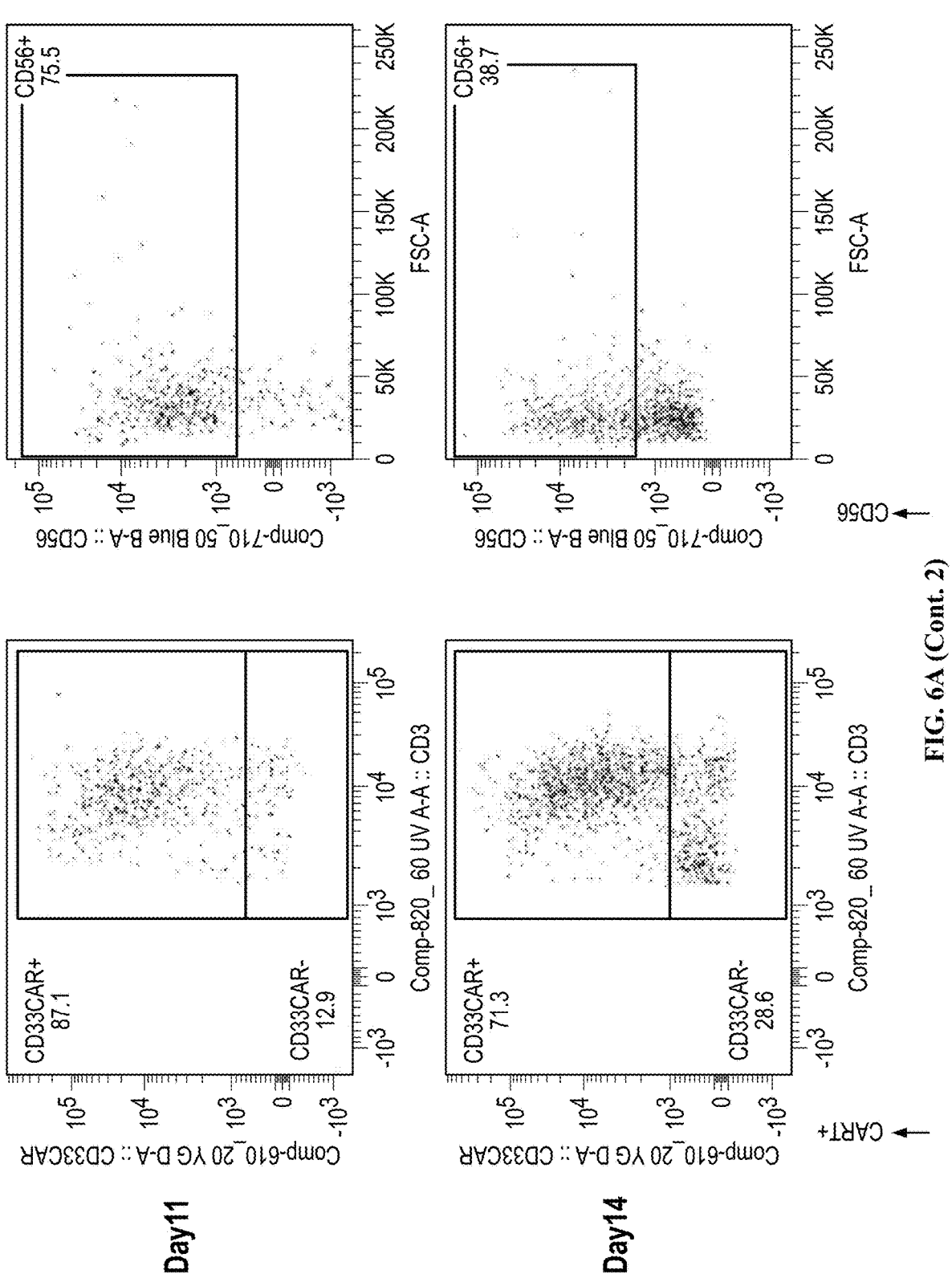
FIG. 6A (Cont. 2)

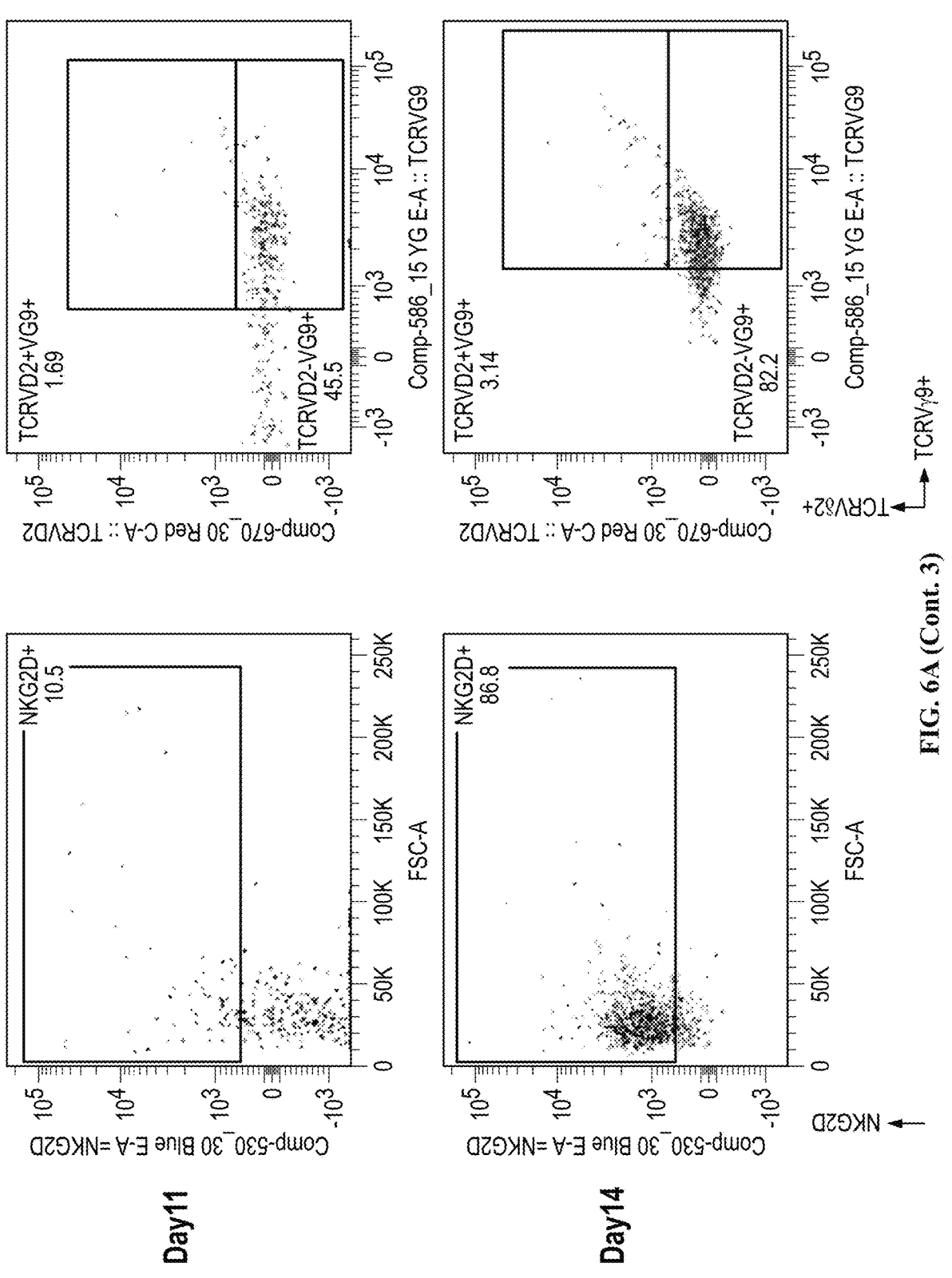
FIG. 6A (Cont. 3)

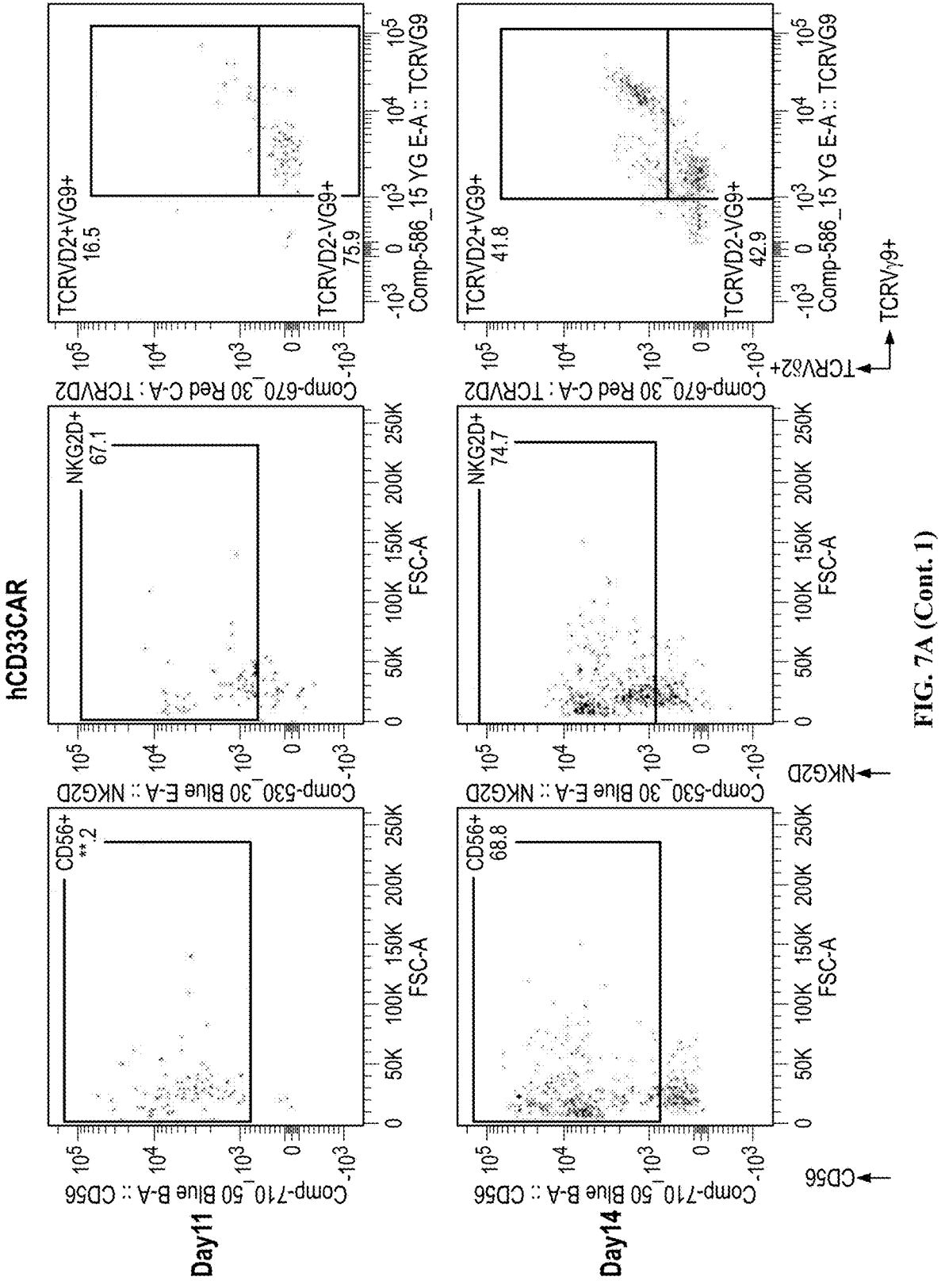
FIG. 7A (Cont.1)

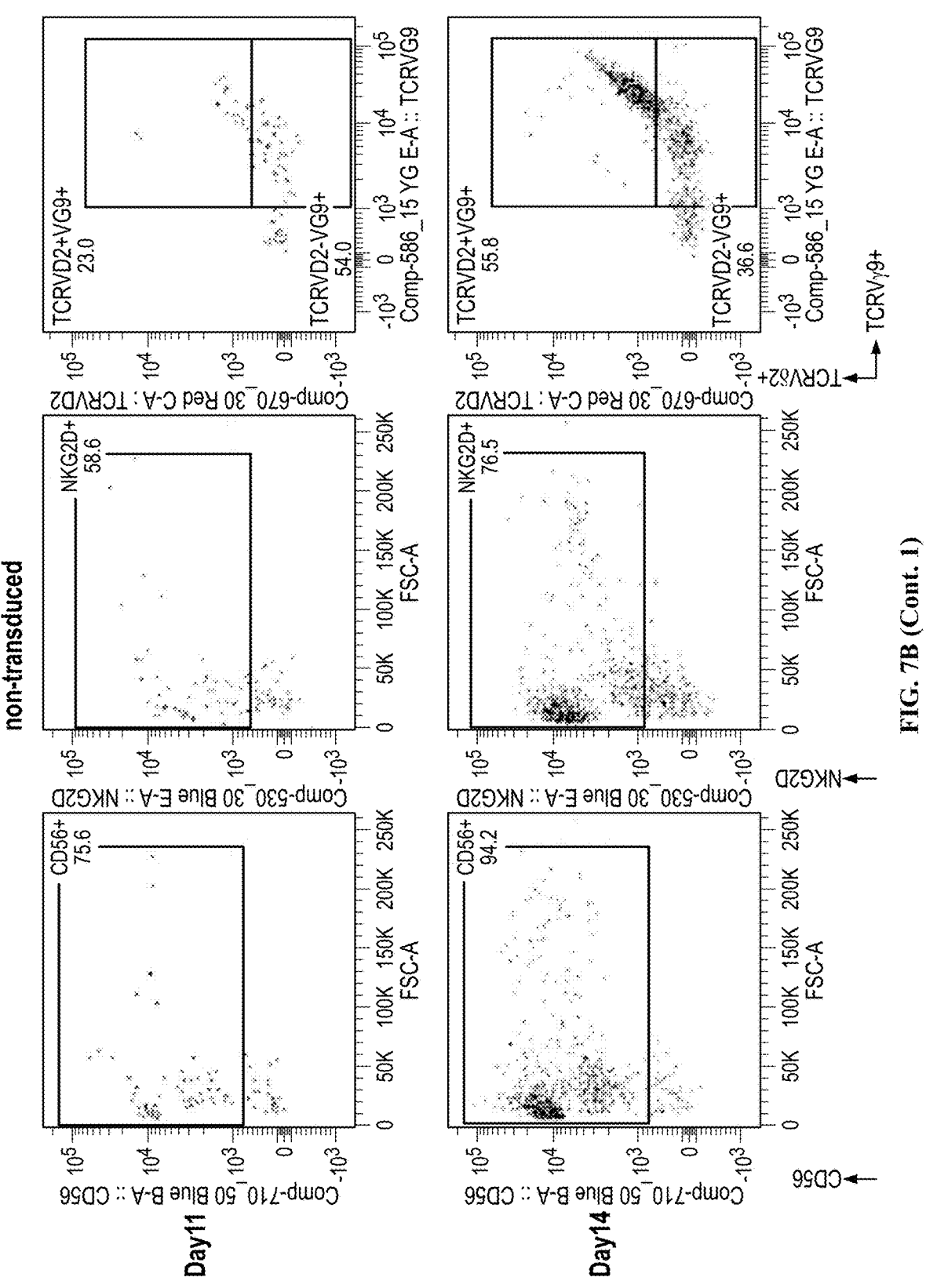
FIG. 7B (Cont. 1)

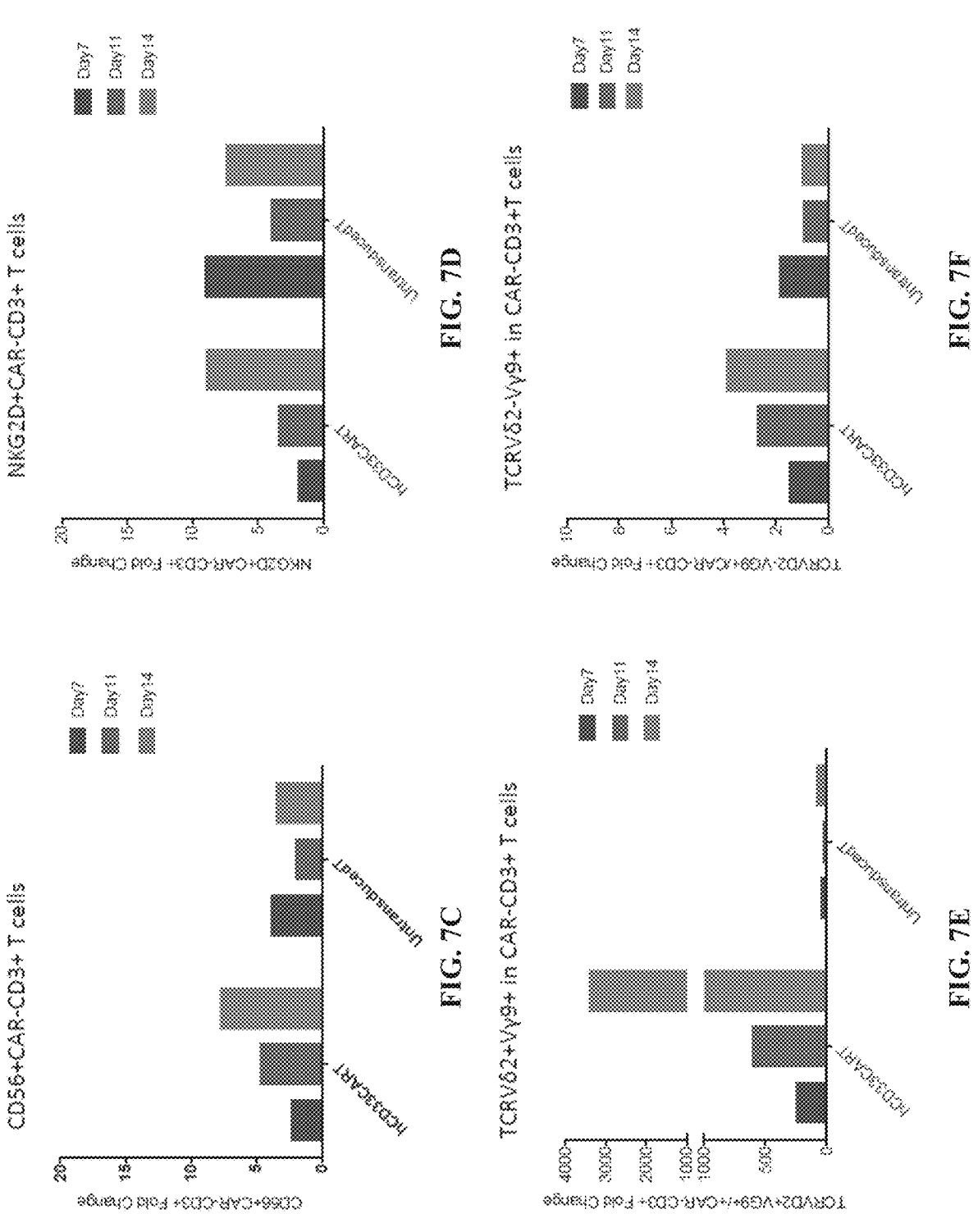

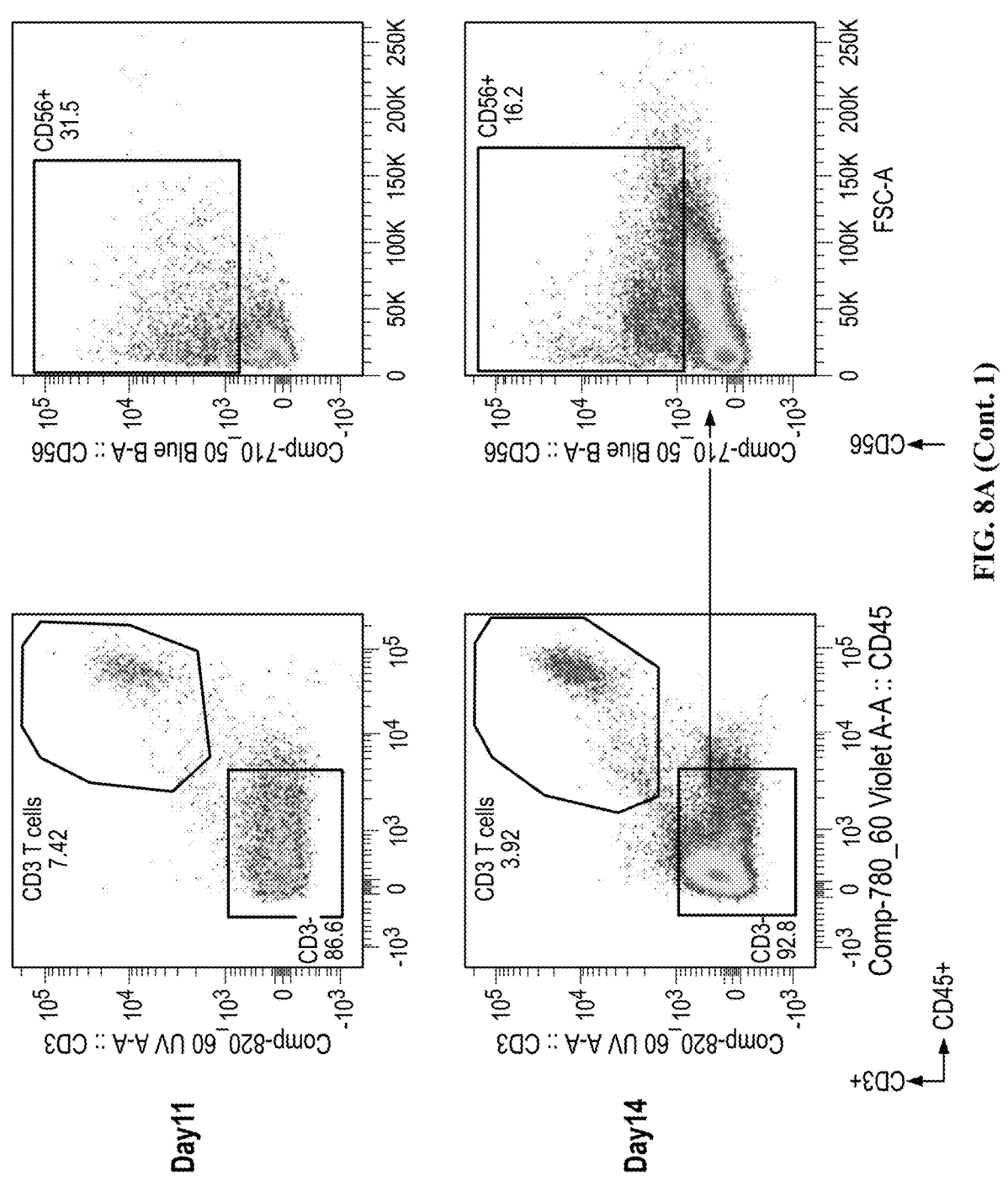
FIG. 8A (Cont. 1)

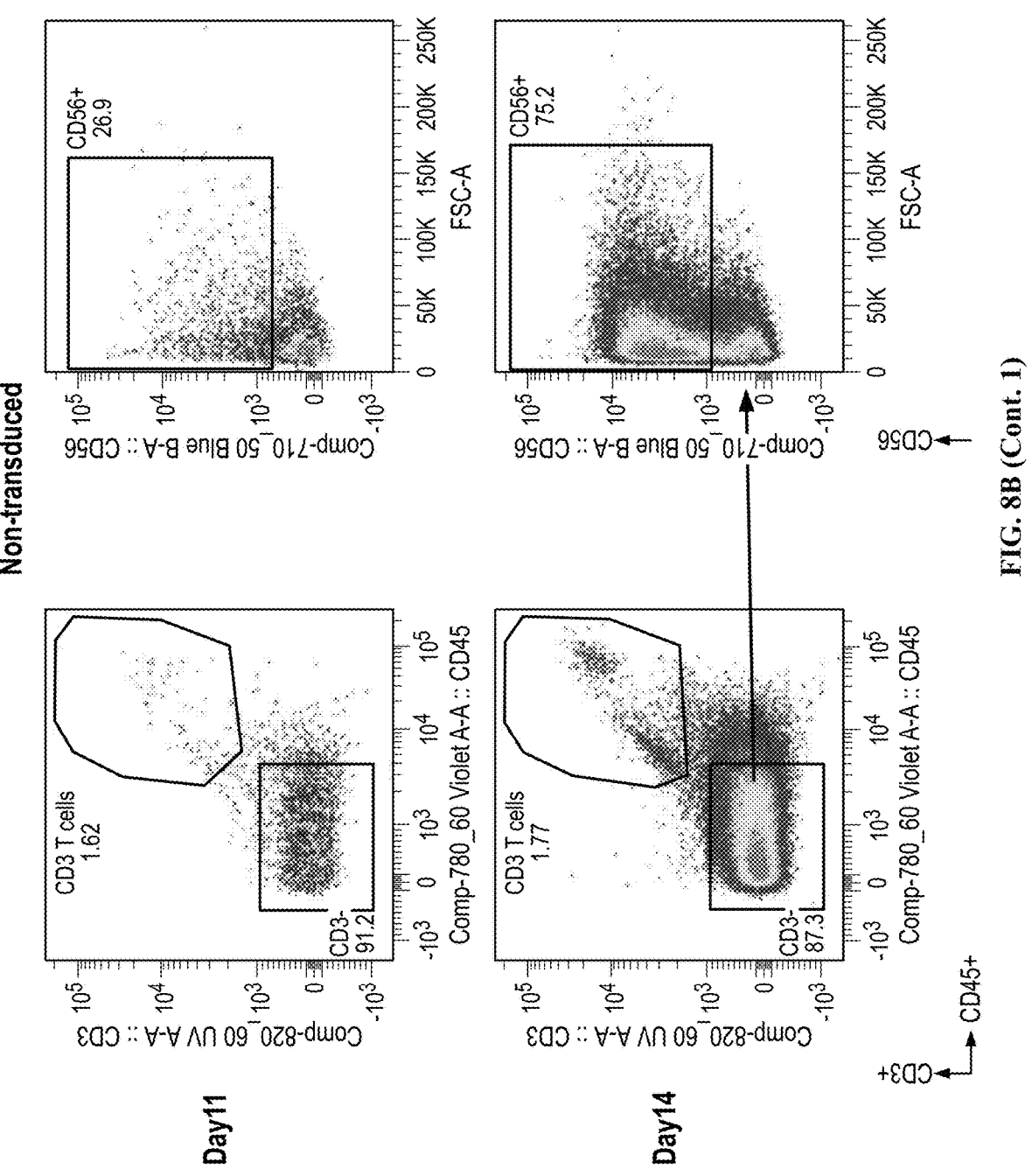
FIG. 8B (Cont. 1)

ARTIFICIAL ANTIGEN PRESENTING CELLS COMPRISING PROTEIN L FOR EXPANDING IMMUNE CELLS FOR IMMUNOTHERAPY

CROSS REFERENCE TO RELATED APPLICATIONS

This application is a United States National Phase Patent Application of International Patent Application Number PCT/US2019/035486, filed on Jun. 5, 2019, which claims the benefit of priority to U.S. Provisional Application No. 62/680,951, filed Jun. 5, 2018, applications which are incorporated by reference herein in their entirety.

BACKGROUND

Adoptive cell therapy (ACT) using chimeric antigen receptor (CAR) T cells, tumor infiltrating lymphocytes (TIL), and/or marrow-infiltrating lymphocytes (MIL) can lead to positive, objective, and durable responses in cancer patients. However, this therapy can involve sophisticated cell processing techniques and equipment. These procedures have introduced technical, regulatory, and logistic challenges to the successful use of CAR T cells, MIL, TIL as a biological therapy. Accordingly, there is a need in the art for improved methods for growing CAR T cells, MIL, and/or TIL for use in adoptive cell therapy.

SUMMARY

Disclosed herein are methods of expanding immune cells for immunotherapy using artificial antigen presenting cells (aAPCs) having on their surface Protein L and/or antibodies (including, but not limited to antibody fragments, such as, for example, F(ab')2, Fab', Fab, and/or scFv) and/or ligands that bind molecules of both the T cell activation pathway and T cell co-stimulation pathway. The disclosed aAPCs can also secrete or express on their cell surface antibodies that bind molecules of the T cell inhibitory pathway. For example, anti-CD3 scFv on the surface of the aAPCs can bind and activate T cells, while anti-CD28 scFv and 4-1BBL on the surface of the aAPCs can provide dual co-stimulation for the T cells resulting in decreased levels of the markers CD25, TIM3, LAG3, and PD1. This is a less costly and more efficient alternative to peripheral blood mononuclear cells (PBMCs) and cytokine treatments that result in better quality T cell for adoptive transfer back into patients.

In some embodiments, the disclosed aAPCs secrete an antibody (e.g. anti-PD1 or PDL1) that interferes with suppression of T cells, e.g. by ligation of PD1 with PDL1. This suppression is a normal physiologic immune response meant to prevent over-activation of T cells. However, cancer cells have co-opted this suppression pathway as a means to evade immune recognition and tumor killing. This system is a less costly, more efficient and more rapid alternative to peripheral blood mononuclear cells (PBMCs) and cytokine treatments. The system is less costly because a renewable resource replaces the need for cytokines, antibodies for activation, and PBMC feeders. The faster production time is also clinically meaningful considering that patients have to wait a few months for production of their cells, which can be a difficult task for patients with metastatic cancer. Also, extended culture often produce terminally differentiated T cells that have limited function and persistence when adoptively transferred back into patients. The shorter culture time therefore allows the ability to infuse a T cell product that is more physiologic and tumor-reactive.

Also disclosed herein are methods of increasing the purity of CAR T cells in a population of immune cells, comprising providing an artificial antigen presenting cell (aAPC) comprising a cell having a membrane, wherein the aAPC expresses Protein L, and comprises Protein L on its membrane; and incubating the immune cell population with the aAPC for at least 8, 9, 10, 11, 12, 13, 14, 15, 16, 17, 18, 19, 20, 21, 22, 23, 24, 26, 28, 30, 32, 34, 36, or 48 hours; wherein the aAPC induces the CAR T cells to proliferate The details of one or more embodiments of the invention are set forth in the accompanying drawings and the description below. Other features, objects, and advantages of the invention will be apparent from the description and drawings, and from the claims.

DESCRIPTION OF DRAWINGS

Figure 1:
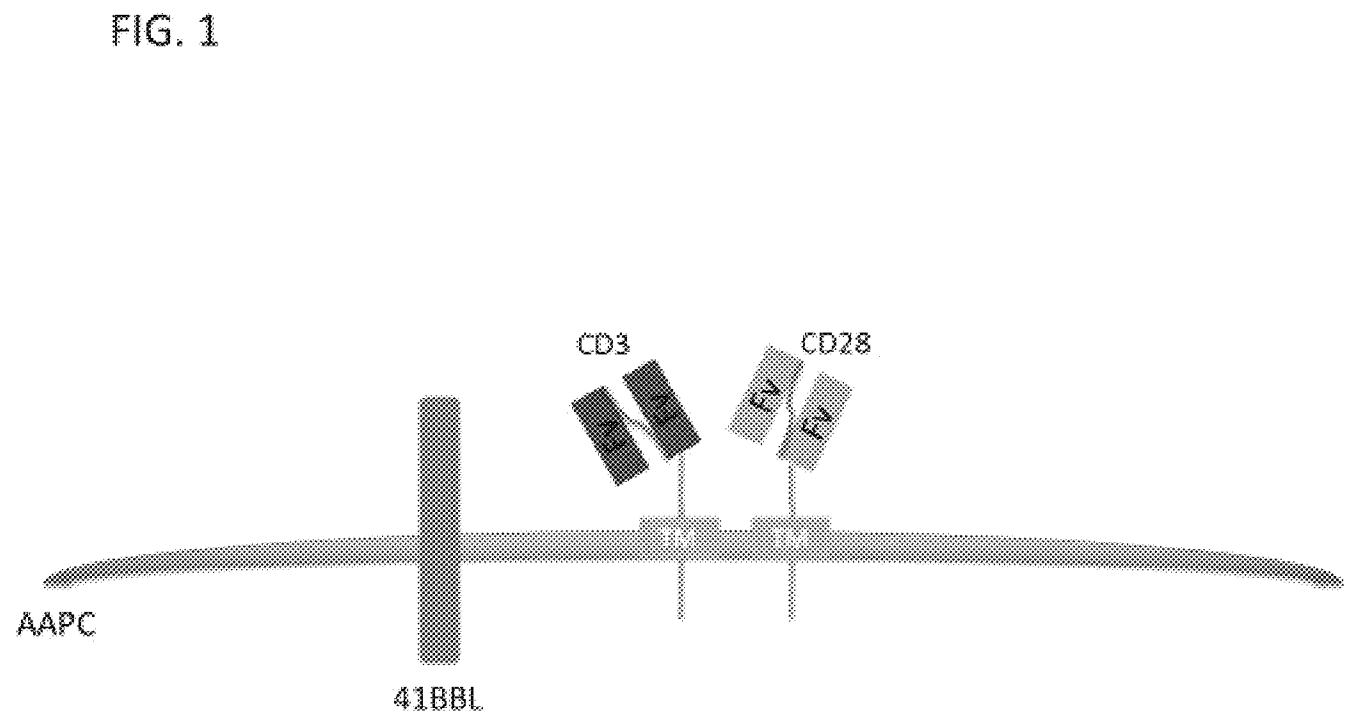

FIG. 1 shows a schematic of an artificial antigen present cell (aAPC) for T cell expansion. The aAPC bind and active the T cell by anti-CD3 membrane bound scFv. The aAPC also co-stimulate the T cells by anti-CD28 scFv and the 41BB ligand (41BBL). The results in expansion of T cells.

Figure 2:
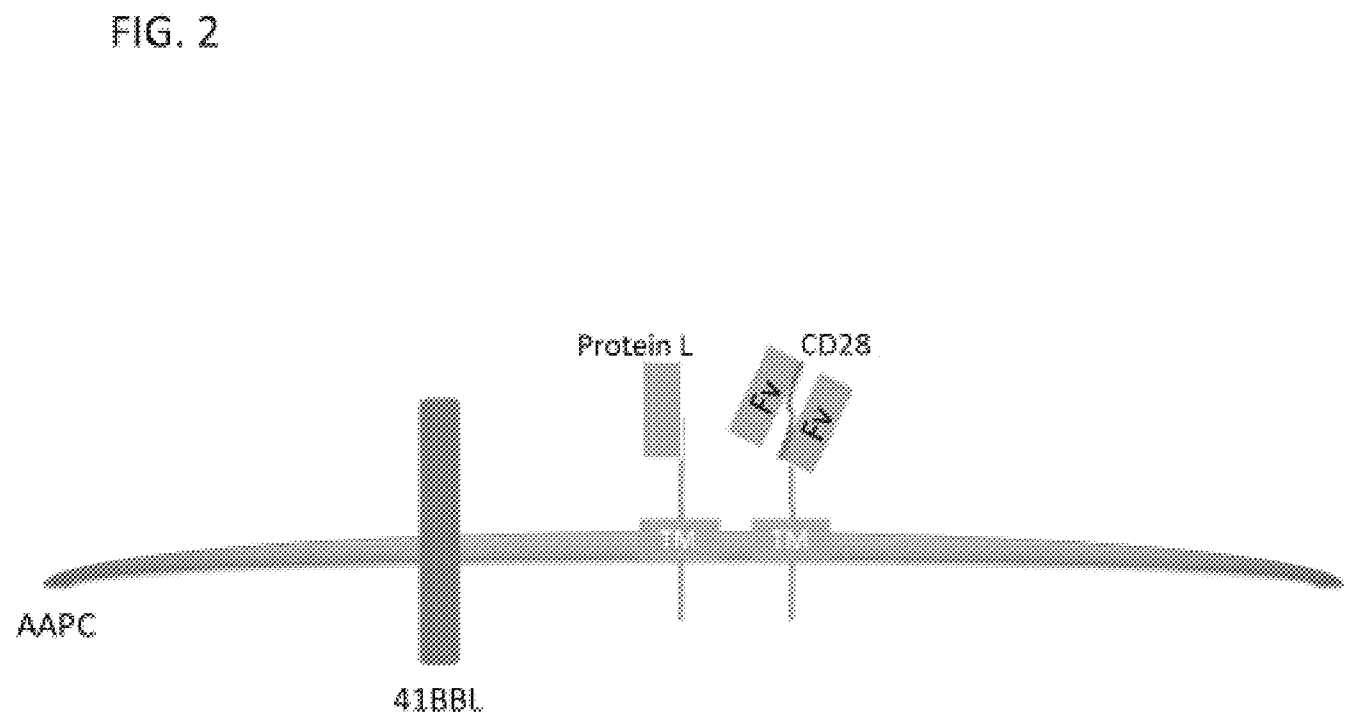

FIG. 2 shows a schematic of an aAPC for selective CAR T cell expansion. By replacing the anti-CD3 membrane bound scFv with Protein L this allows activation of only CAR T cells thereby supporting the selective expansion and enrichment of CAR T cells in a mixed population of CAR+ and CAR− T cells.

FIG. 4 shows Human CD33+ CAR T cells and non-transduced human normal CD3+ T cells from the same donor that were co-cultured with irradiated K562 cells expressing protein L for 14 days, and the portion of human CD33 CAR T positive cells can be maintained and also can be increased with K562proteinL AAPCs.

FIGS. 5A and 5B show CD8+CAR+ T cells increased 5-6 times more than CD4+CAR+ T cells on day 11 and day14 in human CD33CAR T group. FIGS. 5C and 5D show CD8+ T cells increasing more than CD4+ T cells can also be observed on CAR-CD3+ population in CAR T group.

FIG. 6A shows flow dot plots are demonstrating the gating of CD56, NKG2D, TCRVδ2+ Vγ9+ and TCRVδ2-Vγ9+ expression on CD3+ CAR+ T cell in human CD33 CAR T group. FIGS. 6B and 6C show that this donor CAR+ T cells started with more than 60% of CD56 and NKG2D positive cells with K562proteinL AAPCs on day0, CD56, the percentage was reduced by day14, but in absolute cell number, specially, both CD56 and NKG2D were going up by the end of co-culture on day14. FIGS. 6D and 6E show that Gamma delta T cells are the minor population of T cells from human peripheral blood, which do not require MHC class I or II antigen presenting to γδ T cells while they perform their adaptive immune function. TCRVδ2+Vγ9+ are the major population of γδ T cells that not only have the cytotoxicity but also can act as γδ T-APC to present antigen to up αβ T cells. In the co-culture with K562proteinL AAPCs, TCRVδ2+Vγ9+ increased significantly by day14.

FIGS. 7A, 7B, 7C, 7D, 7E, and 7F show Biomarkers on CD3+CAR− T cells. FIGS. 7A and 7B show the two panels are demonstrating the gating of CD56, NKG2D, TCRVδ2+ Vγ9+ and TCRVδ2-Vγ9+ expression on CD3+ CAR− T cells from human CD33CAR t and non-transduced t cell group respectively. FIGS. 7C and 7D show the K563proteinL AAPC can increase CD56 and NKG2D expression in CAR-CD3+ and non-transduced CD3+ T cells. FIGS. 7E and 7F show that the AAPCs also significantly increased TCRVδ2+Vγ9+ and TCRVδ2-Vγ9+ on CAR-CD3+ t cells and CD3+ from non-transduced t cells, specifically had the most increase in CAR t group.

FIGS. 8A and 8B show CD56 expressed on CD3− cells, specifically showing big increase on CD3− cells of non-transduced group. FIG. 8C shows the fold change from non-transduced cells had more than 50,000 increase.

DETAILED DESCRIPTION

Figure 3:
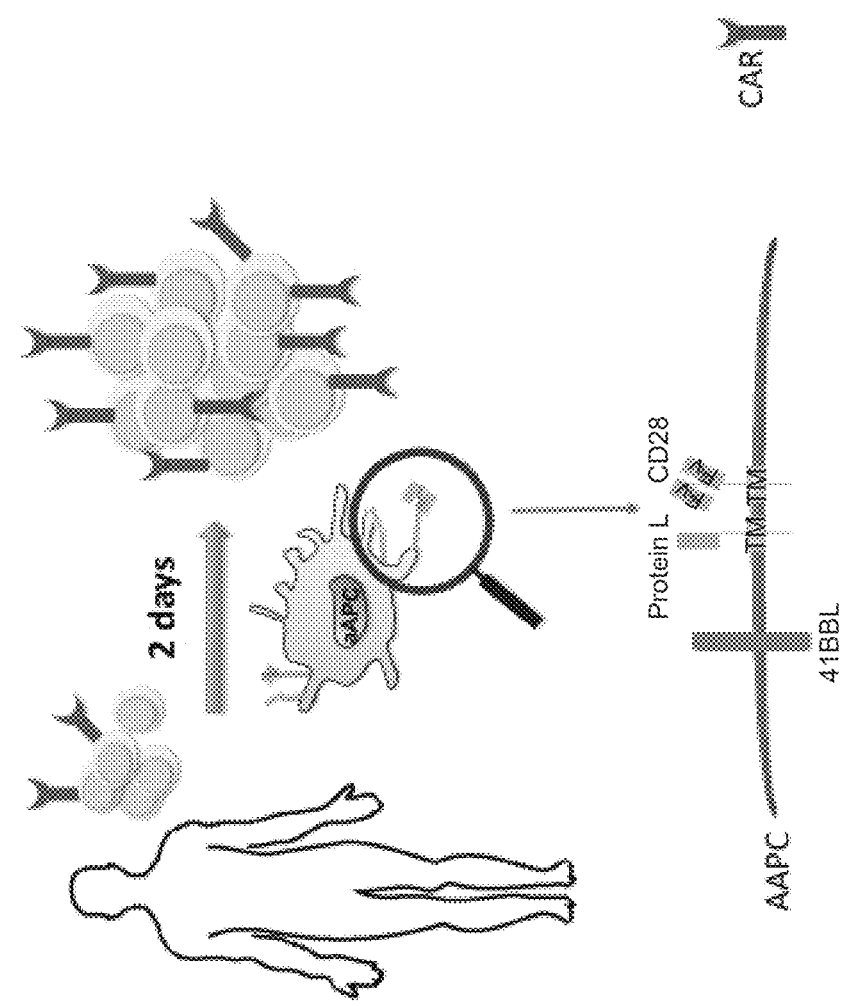
FIG. 3 shows a schematic of aAPC expansion of CAR T cells. Protein L activates only CAR T cells thereby supporting the selective expansion and enrichment of CAR T cells in a mixed population of CAR+ and CAR− T cells.

Disclosed herein are methods for expanding an immune cell for use in immune therapy. The disclosed methods comprise providing an artificial antigen presenting cell (aAPC) comprising a cell having a membrane, wherein the aAPC expresses Protein L, and comprises Protein L on its membrane. Protein L is a bacterial protein from *Peptostreptococcus magnus* that binds to the kappa light chain of antibodies and is therefore its binding is not limited to full antibodies, but can also bind antibody fragments such as scFv and Fab fragments. Of note, the ability to bind the kappa light chain allows for the aAPC to bind the antigen-binding domain of CAR T cells. Because Protein L is not native to mammals, Protein L can be used as a target for antibody based detection or purification methods. For example, an antibody specific for Protein L can be used to detect or isolate CAR T cells that are bound by Protein L. Accordingly, in one aspect, disclosed herein are methods for expanding an immune cell for use in immune therapy comprising providing an artificial antigen presenting cell (aAPC); wherein the aAPC comprises a cell membrane, wherein the aAPC expresses Protein L, and comprises Protein L on its membrane; and contacting the isolated immune cell with an effective amount of the aAPC to expand the immune cell in an amount effective for immunotherapy.

As noted above, Protein L is not a native protein to mammalian cells, and thus its ability to bind to kappa (κ)

light chains can be used as a marker for cells bound to Protein L, such as, for example CAR T cells. In one aspect, the binding of the Protein L marker can be used to identify, expand, enrich, and/or purify an immune cell population for cells bound by Protein L (for example, CAR T cells). Protein L detection can be achieved via antibodies that specifically bind to Protein L. Therefore, any purification and detection methods employing antibodies (including tagged antibodies for use in flow cytometry, ELISAs, ELIspots, and florescence acquired cell sorting (FACS)) can be used to identify, detect, enrich, and/or purify cell bound to protein L. In one aspect, disclosed herein are method for increasing the purity of a specific subset population of immune cells (such as, for example CAR T cells, TILs, MILs, NK cells, NK-T cell, cytokine-induced memory NK cells, a cytokine-induced killer (CIK) cells, and/or γδ T cells) in a mixed population of immune cells (such as, for example, a population of immune cells comprising CD4 T cells, CD8 T cells, NK cells, CIK cells, γδ T cells, macrophage, and/or B cells), comprising a) providing an artificial antigen presenting cell (aAPC) comprising a cell having a membrane, wherein the aAPC expresses Protein L, and comprises Protein L on its membrane; and b) incubating the immune cell population with the aAPC; wherein the aAPC induces only the CAR T cells to proliferate. In one aspect, the method can further comprise separating the CAR T cells bound to Protein L via fluorescence acquired cell sorting (FACS).

It is understood and herein contemplated that by incubating the aAPC in an immune cell population, the aAPC will selectively stimulate and induce proliferation of the cells to which they bind (for example, CAR T cells). As the incubation time increases so too does the purity of the aAPC bound cell population. Thus, in one aspect, disclosed herein are methods of increasing the purity of immune cells (such as, for example, CAR T cells), wherein the immune cells are incubated with the aAPC for at least 8, 9, 10, 11, 12, 13, 14, 15, 16, 17, 18, 19, 20, 21, 22, 23, 24, 26, 28, 30, 32, 34, 36, 48, 60 hours, 3, 4, 5, 6, 7, 8, 9, 10, 11, 12, 13, 14, 15, 16, 17, 18, 19, 20, 21, 28, or 30 days.

It is understood and herein contemplated that the immune cell used in the disclosed methods can be isolated from a subject receiving the immune therapy (an autologous donor source), from a type match donor source (i.e., syngeneic), from a non-type matched donor source of the same species (i.e, an allogeneic source), a donor of a different species (xenogeneic source), or cell line. In one aspect, the immune cell (i.e., the cell of specific subset immune cell population to be expanded) can be a chimeric antigen receptor (CAR) T cell, tumor infiltrating lymphocyte (TIL), or marrow-infiltrating lymphocyte (MIL). In other aspects, the immune cell can comprise a natural killer (NK) cell, an NK-T cell, a cytokine-induced memory NK cell, a cytokine-induced killer (CIK) cell, or a γδ T cell.

In one aspect, it is understood and herein contemplated that the aAPC expressing Protein L can be further engineered to enhance the aAPC ability to bind T cells and stimulate proliferation. For example, an antibody or antibody fragment (such as, for example, scFv) that binds to the T cell receptor (CD3) or that binds to a co-stimulatory molecule on T cells (for example, CD28 or 4-1BB). Where the immune cell to be expanded is an NK cell, the co-stimulator molecule ca be CD80 or CD86. Accordingly, in one aspect disclosed herein are methods of methods for expanding an immune cell for use in immune therapy or methods for increasing the purity of CAR T cells said methods comprising providing an aAPC; wherein the aAPC comprises Protein L on its cell membrane and wherein the aAPC further comprises one or more antibodies, antibody fragments (such as, for example, scFv), or ligands that bind a co-stimulatory molecule on T-cells (such as, for example, CD28 and/or 4-1BB), one or more scFv that selectively bind CD3, and/or a combination thereof on the cell membrane.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

As used herein, the term "antibody or fragments thereof" encompasses chimeric antibodies and hybrid antibodies, with dual or multiple antigen or epitope specificities, and fragments, such as F(ab')2, Fab', Fab, scFv, and the like, including hybrid fragments. Thus, fragments of the antibodies that retain the ability to bind their specific antigens are provided. For example, fragments of antibodies which maintain CD3, CD28, CD137, PD1, CTLA4, LAG3, TIM3, BTLA, CD160, 2B4, A2aR, and KIR binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual.* Cold Spring Harbor Publications, New York, (1988)).

Also included within the meaning of "antibody or fragments thereof" are conjugates of antibody fragments and antigen binding proteins (single chain antibodies).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The term "specifically binds", as used herein, when referring to a polypeptide (including antibodies) or receptor, refers to a binding reaction which is determinative of the presence of the protein or polypeptide or receptor in a heterogeneous population of proteins and other biologics.

Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

In one aspect, the aAPCs expressing Protein L disclosed herein can secrete or express surface bound antibodies or antibody fragments that bind molecules of the T cell inhibitory pathway. In some embodiments, the disclosed aAPCs secrete an antibody or antibody fragment (for example, an scFv) that interferes with suppression of T cells, e.g. by ligation of PD1 with PDL1 such as, for example, use of an anti-PD1 or PDL1 antibody or antibody fragment. This suppression is a normal physiologic immune response meant to prevent over-activation of T cells. However, cancer cells have co-opted this suppression pathway as a means to evade immune recognition and tumor killing. This system is a less costly, more efficient and more rapid alternative to peripheral blood mononuclear cells (PBMCs) and cytokine treatments. The system is less costly because a renewable resource replaces the need for cytokines, antibodies for activation, and PBMC feeders. The faster production time is also clinically meaningful considering that patients have to wait a few months for production of their cells, which can be a difficult task for patients with metastatic cancer. Also, extended culture often produce terminally differentiated T cells that have limited function and persistence when adoptively transferred back into patients. The shorter culture time therefore allows for the ability to infuse a T cell product that is more physiologic and tumor-reactive. In one aspect, other immune cell inhibitory molecule comprises CTLA4, LAG3, TIM3, BTLA, CD160, 2B4, A2aR, PD-1, ICOS, CD25, TIM3, LAG3, PD1, CD40, CD137, OX40, CD2, LFA-1, CD28, CD154, BTLA, CD160, TIM 1, TIM 4, KIR, any glucocorticoid-induced tumor necrosis factor-related receptor (GITR), and/or any combination thereof. Thus, in one aspect, disclosed herein are methods for expanding an immune cell isolated from a subject for autologous immune therapy and/or methods for increasing the purity of CAR T cells said methods comprising a) providing an artificial antigen presenting cell (aAPC) comprising a cell membrane; wherein the aAPC expresses Protein L and comprises Protein L on its cell membrane; wherein the cell secretes one or more single chain variable fragment (scFv) antibodies that bind a T cell inhibitory molecule, or a combination thereof; and b) contacting the isolated immune cell with an effective amount of the aAPC to expand the immune cell in an amount effective for immunotherapy. In one aspect, the aAPC can further comprise on its membrane: one or more scFv that selectively bind an immune cell selective receptor (such as, for example CD3) and one or more scFv or ligands that bind a co-stimulatory molecule on T-cells (such as, for example, CD28 and/or 4-1BB). For example, in one aspect disclosed herein are methods for expanding an immune cell isolated from a subject for autologous immune therapy, comprising a) providing an artificial antigen presenting cell (aAPC) comprising a cell membrane; wherein the aAPC expresses Protein L and comprises Protein L on its cell membrane, wherein the cell secretes one or more single chain variable fragment (scFv) antibodies that bind a T cell inhibitory molecule, or a combination thereof, wherein the cell contains on its membrane: one or more scFv that selectively bind CD3 and one or more scFv or ligands that bind CD28 and/or 4-1BB (such as, for example an anti-CD38 scFv and/or 4-BBL); and b) contacting the isolated immune cell with an effective amount of the aAPC to expand the immune cell in an amount effective for immunotherapy.

In one aspect, the methods of expanding immune cells and/or increasing the purity of immune cells can be used for expanding, enriching, and/or purifying CAR T cells, TILs, or MILs which can be used in immunotherapy. It is understood and herein contemplated that the use of said cells can comprise expanding CAR T cells, TILs, or MILs from a tissue from a subject. In one aspect, the CAR T cells, TILs, or MILs may be obtained from any tissue (such as, for example, biopsy, blood, urine, sputum, saliva, tissue lavage) in a subject by any means known in the art (tissue resection, biopsy phlebotomy, core biopsy). Because the tissue sample can be used, it can be advantageous to screen expanded CAR T cells, TILs, or MILs for desired activity (such as, for example, tumoricidal activity via expression of CD107). Thus, in one aspect, disclosed herein are methods for expanding tumor infiltrating lymphocytes for use in immunotherapy, comprising a) providing an artificial antigen presenting cell (aAPC) comprising a cell membrane; wherein the aAPC expresses Protein L and comprises Protein L on its cell membrane; b) expanding MILs and/or TILs from a biopsy of a tumor from a subject; c) screening the MILs and/or TILs for tumoricidal activity using flow cytometry to detect CD107 expression; and d) contacting the tumoricidal MILs and/or TILs with an effective amount of the aAPC to expand the tumoricidal MILs and/or TILs. In one aspect, the disclosed methods can further comprise infusing the expanded tumoricidal MILs and/or TILs into the subject in an effective amount to treat the tumor. In one aspect, the disclosed methods can further comprise aAPC wherein the cell secretes one or more single chain variable fragments (scFv) that bind a T cell inhibitory molecule, or a combination thereof, wherein the cell contains on its membrane one or more scFv that selectively bind CD3 and one or more scFv or ligand that binds a co-stimulatory molecule on T-cells.

It is understood and herein contemplated that the expansion of immune cells and/or increasing the purity of immune cells (such as, for example T cells, NK cells, or B cells) including CAR T cells, TILs, and MILs can occur ex vivo, in vitro, or in situ with the expansion occurring outside the subject and administration occurring after expansion. Thus, the aAPC can be provided in culture to be in proximity and come into contact with the immune cells. However, it is understood and herein contemplated that the expansion of immune cells including CAR T cells, TILs, and MILs can also occur in vivo by directly administering aAPC comprising an scFv that binds to a T cell inhibitory molecule, and an scFv recognizing an immune cell receptor (such as, for example) CD3 and scFv or ligands binding to co-stimulatory molecules (such as, CD28 and 4-1BB) directly to the subject in need of treatment. In one aspect the aAPC can be delivered in vivo. When provided in vivo administration (i.e., providing of the aAPC in an in vivo context) can occur through any route through which administration of the cells is appropriate.

The aAPC comprising protein L on the cell surface may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

In one aspect, the aAPC can further comprise on its membrane surface expression of a scFv or ligand that specifically binds a cytokine such as, IL2R, IL7R, IL12R, IL15R, IL18R, IL10R, or any combination thereof.

The aAPC can be derived from any antigen presenting cell including a cell line such as, for example K562, NIH/ 3T3, Chinese hamster ovary (CHO), or Human Embryonic Kidney (HEK) cell line.

It is understood and herein contemplated that the disclosed methods can result in an expanded immune cell. Accordingly, in one aspect disclosed herein are immune cells produced by any method for expanding immune cells disclosed herein.

A number of embodiments of the invention have been described. Nevertheless, it will be understood that various modifications may be made without departing from the spirit and scope of the invention. Accordingly, other embodiments are within the scope of the following claims.

Figure 4A:
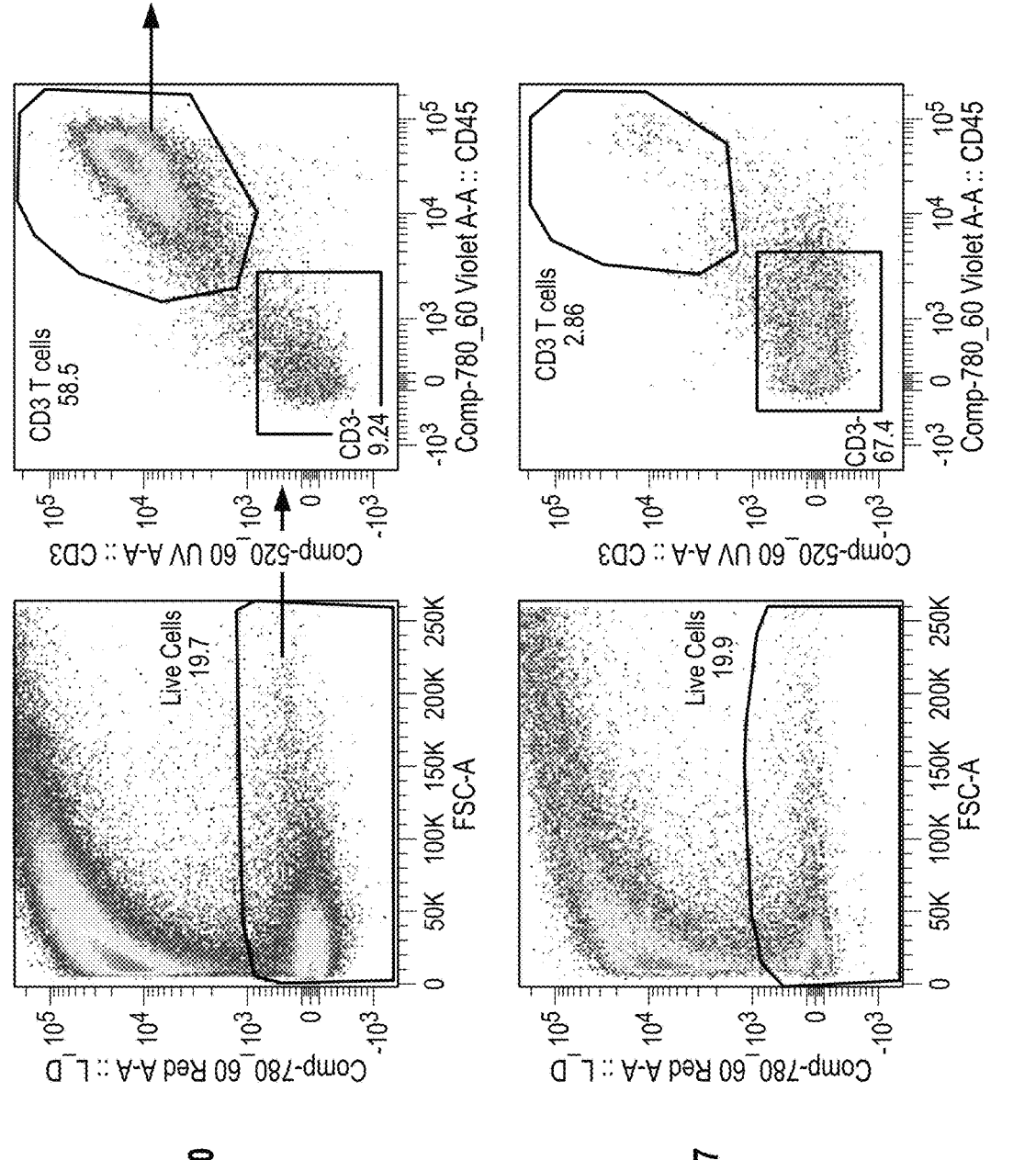
FIG. 4A shows flow dot plots showed the gating strategy from live cells, CD3+ T cells, to CAR+ or CAR− T cells, then gated on CD4+ and CD8+ on either CAR+ or CAR− T cells on day0, day7, day11 and day14.
Figure 4B:
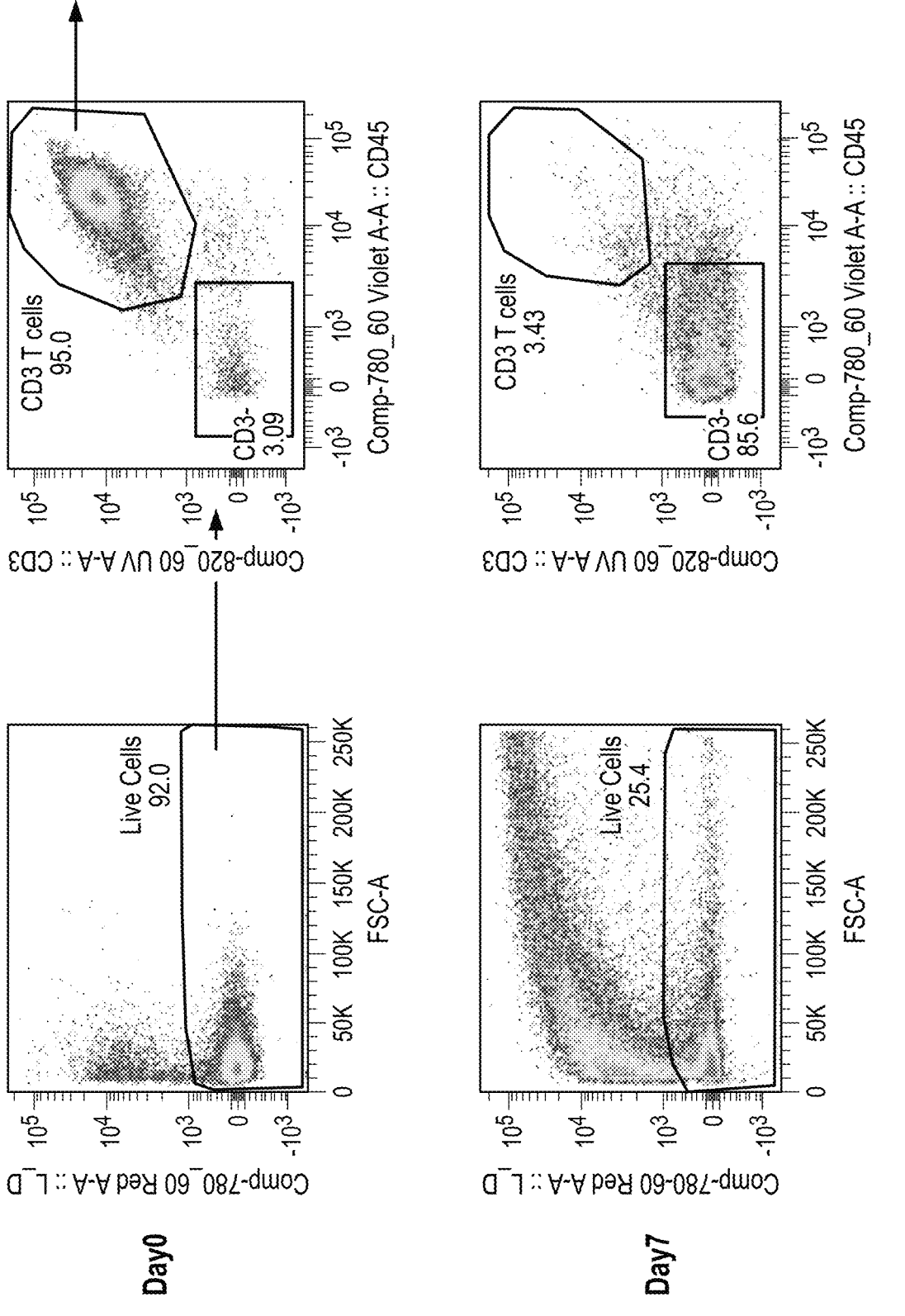
FIG. 4B shows the same gating scheme applied to non-transduced normal T cells from the same donor as a control.
Figures 4C, 4D, 4E, 4F:
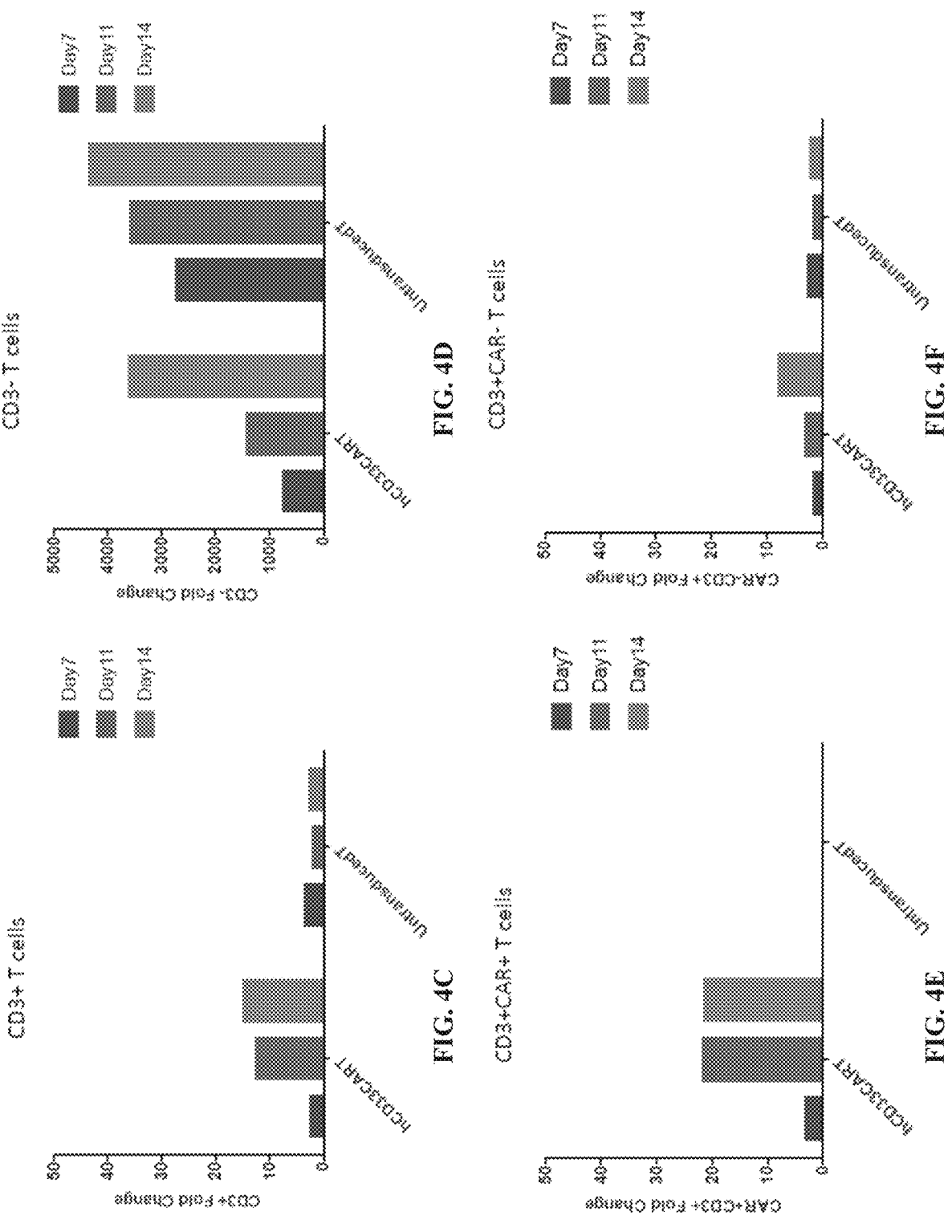
FIG. 4C shows that K562proteinL AAPCs increased more CD3 expression in CD33CAR T cell than non-transduced T cell group even both groups did not have significant CD3 T cell expansion in general.
FIG. 4D shows both human CD33CAR T and non-transduced t cells could not turn up the CD3 expression where the starting cells were ~90% of CD3+ T cells instead CD3 negative cells were expanded.
FIGS. 4E and 4F show K562proteinL AAPCs certainly increased the CAR+ T cell portion in CD33 CAR T group which increased from 50% to 73% by day 14. Additionally, CD33 CAR T cells also saw a 8-10 fold increase relative to non-transduced cells as well as the starting population size. Nevertheless, the AAPCs could not have enough signal to activate CD3. It suggests the co-culture should have included T cell co-stimulatory signal to activate T cell signaling pathway and proliferate CD3+ T cells and at the same time having protein L for the expansion of CAR specific T cells.

To show test the effect of ProteinL expansion on CAR T cells, human CD33+ CAR T cells and non-transduced human normal CD3+ T cells from the same donor that were co-cultured with irradiated K562 cells expressing protein L for 14 days. The portion of human CD33 CAR T positive cells can also be maintained and increased with K562proteinL AAPCs. As shown in FIG. 4A-D, K562proteinL AAPCs increased more CD3 expression in CD33CAR T cell than non-transduced T cell group even both groups did not have significant CD3 T cell expansion in general. Interestingly, in both human CD33CAR T and non-transduced t cells could not turn up the CD3 expression where the starting cells were ~90% of CD3+ T cells instead CD3 negative cells were expanded. K562proteinL AAPCs certainly increased the CAR+ T cell portion in CD33 CAR T group which increased from 50% to 73% by day 14 (FIGS. 4E and 4F). Additionally, CD33 CAR T cells also saw an 8-10-fold increase relative to non-transduced cells as well as the starting population size. Nevertheless, the AAPCs could not have enough signal to activate CD3. It suggests the co-culture should have included T cell co-stimulatory signal to activate T cell signaling pathway and proliferate CD3+ T cells and at the same time having protein L for the expansion of CAR specific T cells.

Figures 5A, 5B, 5C, 5D:
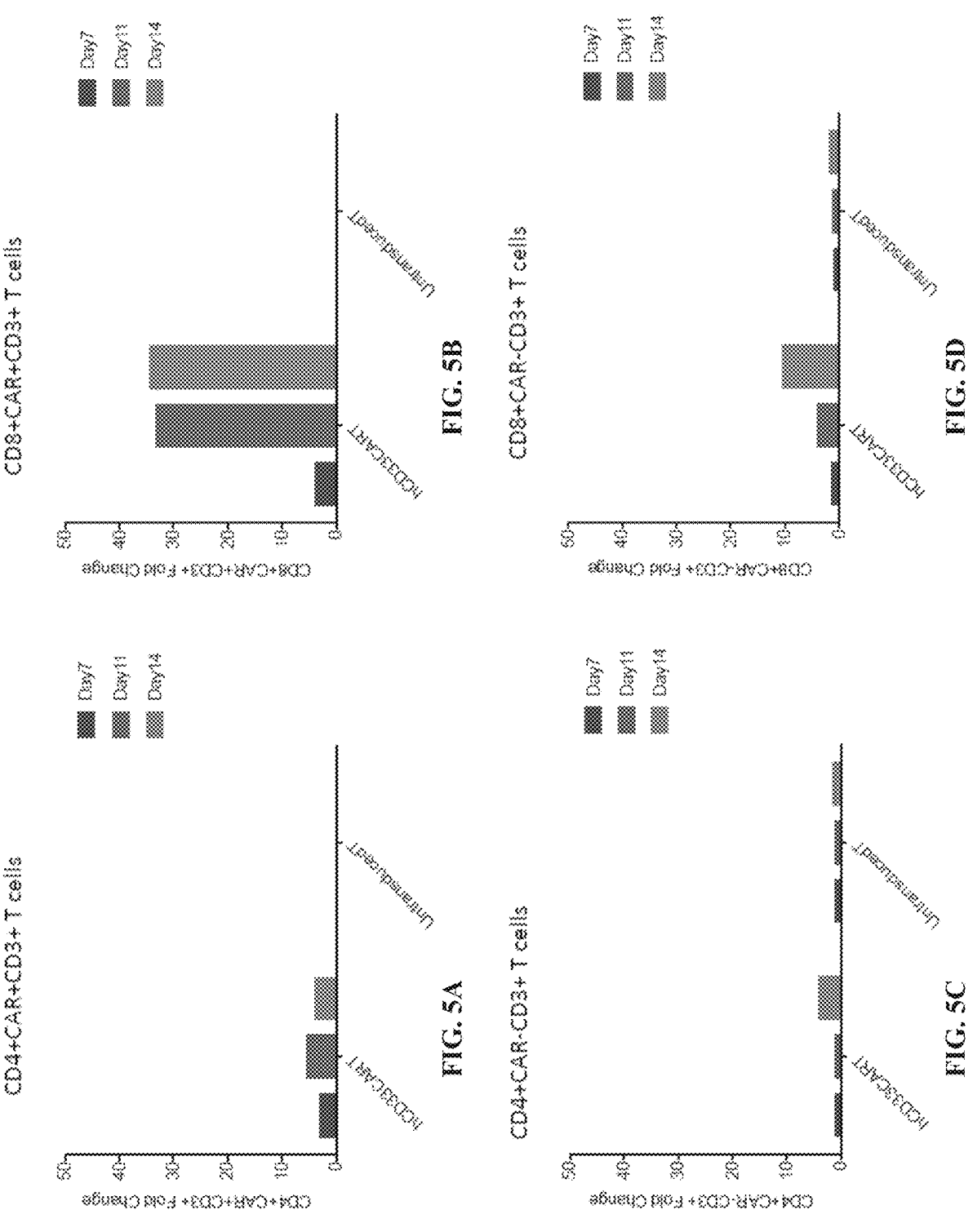
FIGS. 5A, 5B, 5C, and 5D show K562proteinL AAPCs can increase CD8+CAR+ T cells better than CD4+CAR+ T cells.

K562proteinL AAPCs also increased CD8+CAR+ T cells better than CD4+CAR+ T cells. CD8+CAR+ T cells increased 5-6 times more than CD4+CAR+ T cells on day 11 and day 14 in human CD33CAR T group (FIGS. 5A and 5B). Additionally, it was observed in the CAR-CD3+ population in CAR T group that CD8+ T cells increased more than CD4+ T cells.

Figure 6A:
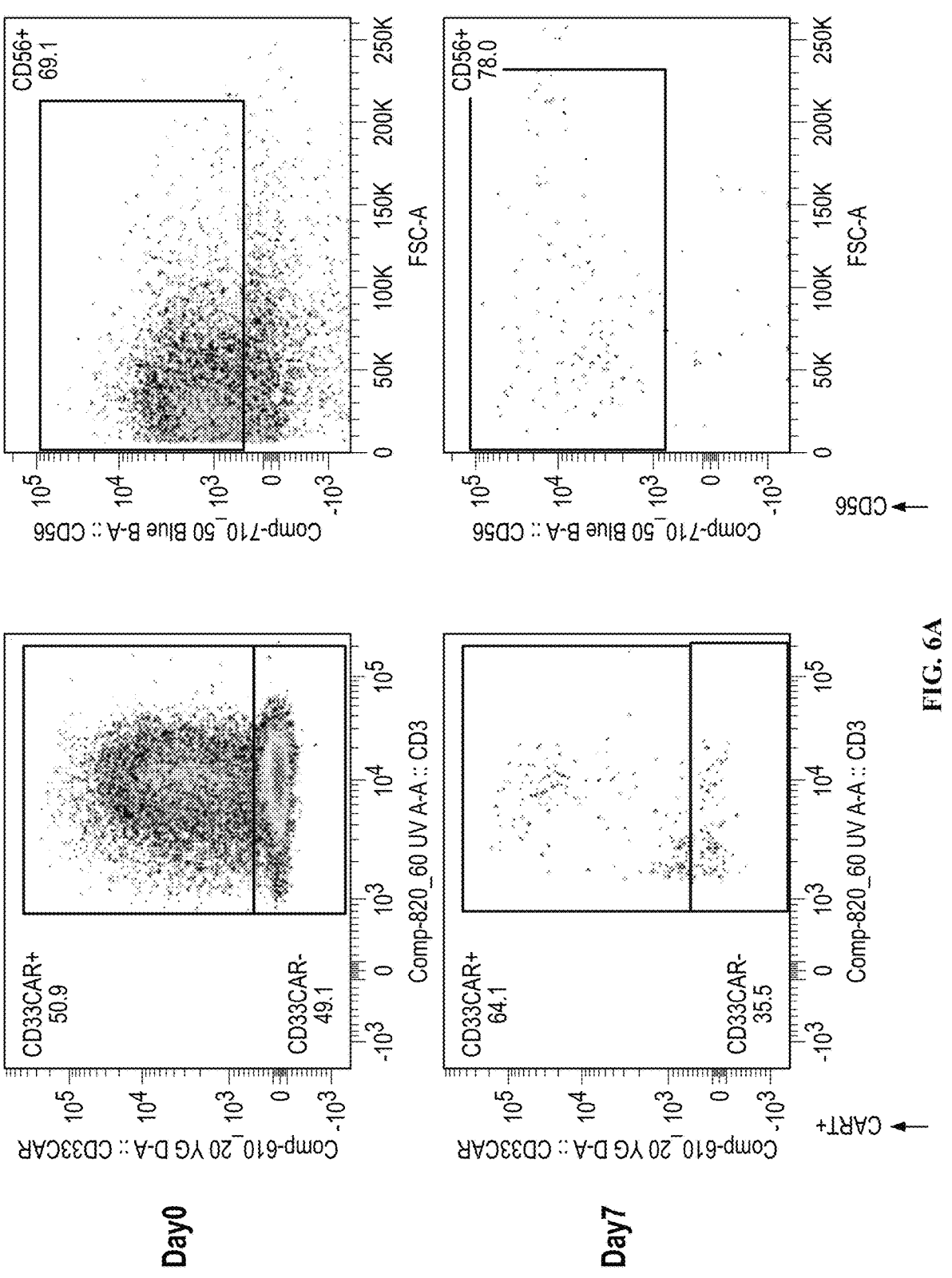
FIGS. 6A, 6B, 6C, 6D, and 6E show biomarkers on CD3+CAR+ T cells.
Figures 6B, 6C, 6D, 6E:
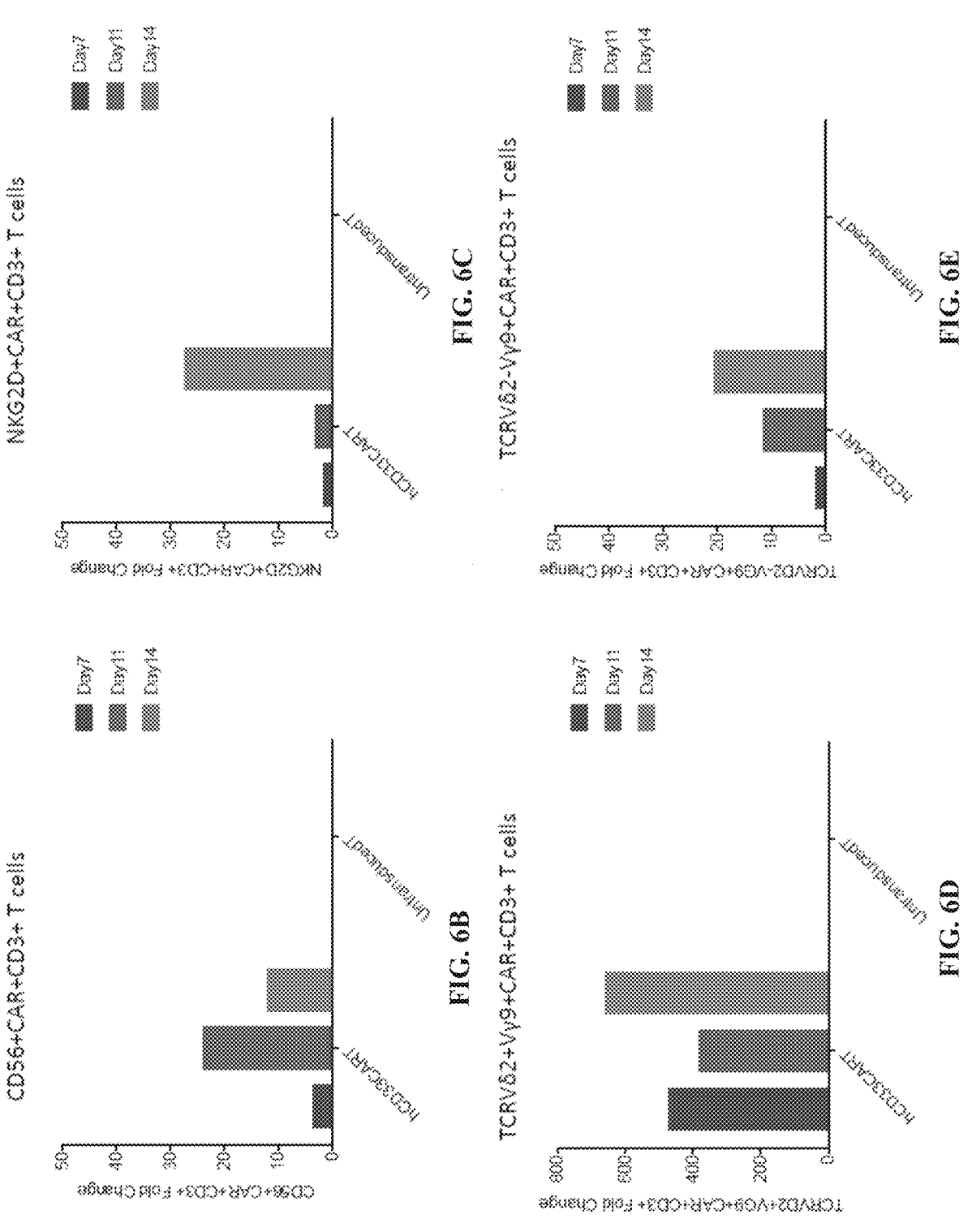

The biomarkers on CD3+CAR+ T cells was also investigated. Flow dot plots were generated demonstrating the gating of CD56, NKG2D, TCRVδ2+Vγ9+ and TCRVδ2-Vγ9+ expression on CD3+CAR+ T cell in human CD33 CAR T group (FIG. 6A). As shown in the analysis, donor CAR+ T cells started with more than 60% of CD56 and NKG2D positive cells with K562proteinL AAPCs on day0 (FIGS. 6B and 6C). Additionally, CD56, the percentage was reduced by day14, but in absolute cell number, specially, both CD56 and NKG2D were going up by the end of co-culture on day14. Interestingly, were the findings relating to δγ T cells (the minor population of T cells from human peripheral blood, which do not require MHC class I or II antigen presenting to δγ T cells while they perform their adaptive immune function) (FIGS. 6D and 6E). TCRVδ2+Vγ9+ are the major population of δγ T cells that not only have the cytotoxicity but also can act as γδ T-APC to present antigen to up αβ T cells. In the co-culture with K562proteinL AAPCs, TCRVδ2+Vγ9+ increased significantly by day14.

Figure 7A:
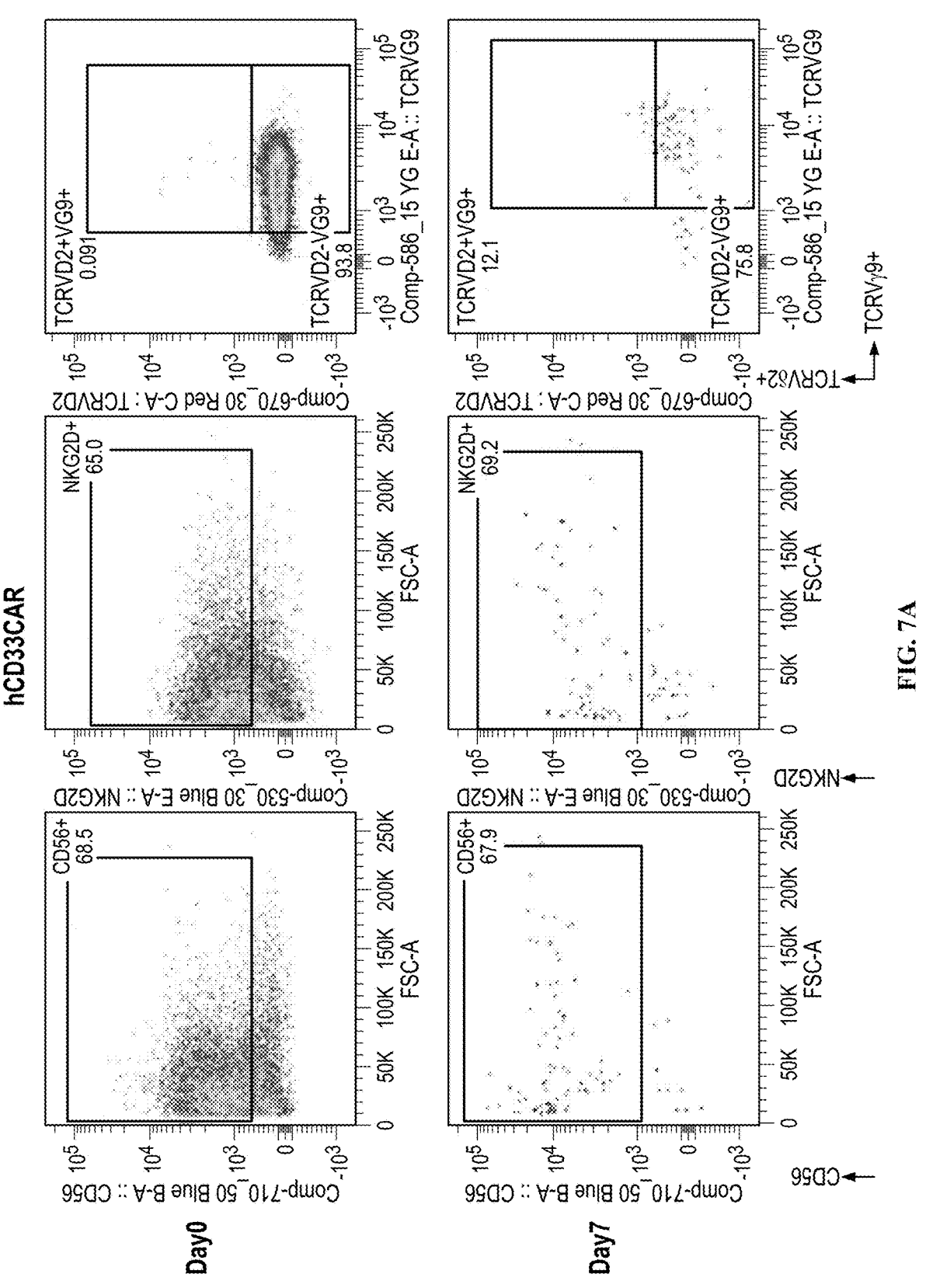
Figure 7B:
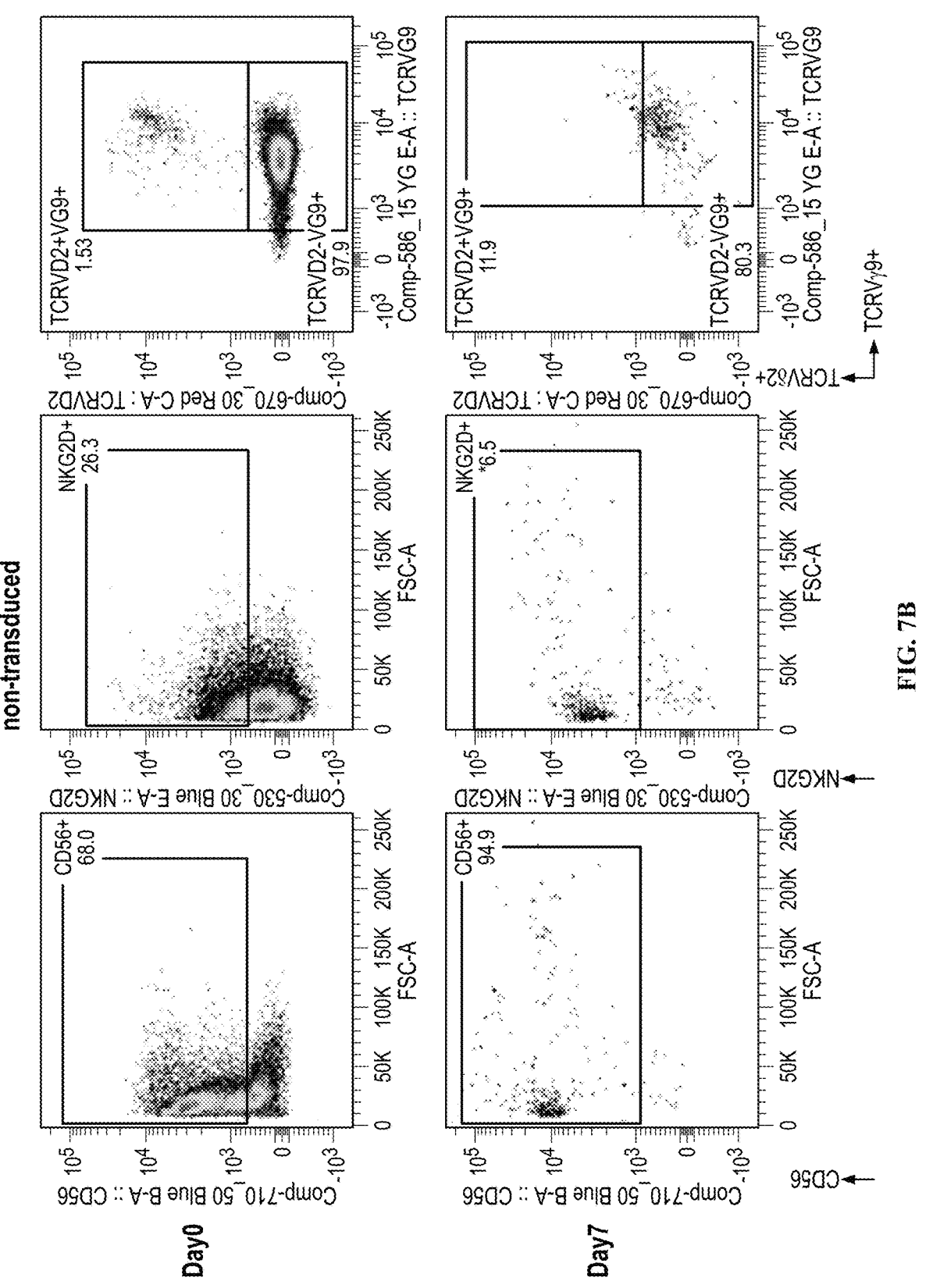

CD3+ CAR− T cells from human CD33CAR T and non-transduced T cell group respectively were analyzed for biomarker expression including CD56, NKG2D, TCRVδ2+Vγ9+ and TCRVδ2-Vγ9+ expression (FIGS. 7A and 7B). The K563proteinL AAPC can increase CD56 and NKG2D expression in CAR-CD3+ and non-transduced CD3+ T cells (FIGS. 7C and 7D). As shown in FIGS. 7E and 7F the AAPCs also significantly increased TCRVδ2+Vδ9+ and TCRVδ2-Vδ9+ on CAR-CD3+ t cells and CD3+ from non-transduced t cells, specifically had the most increase in CAR t group.

Figure 8A:
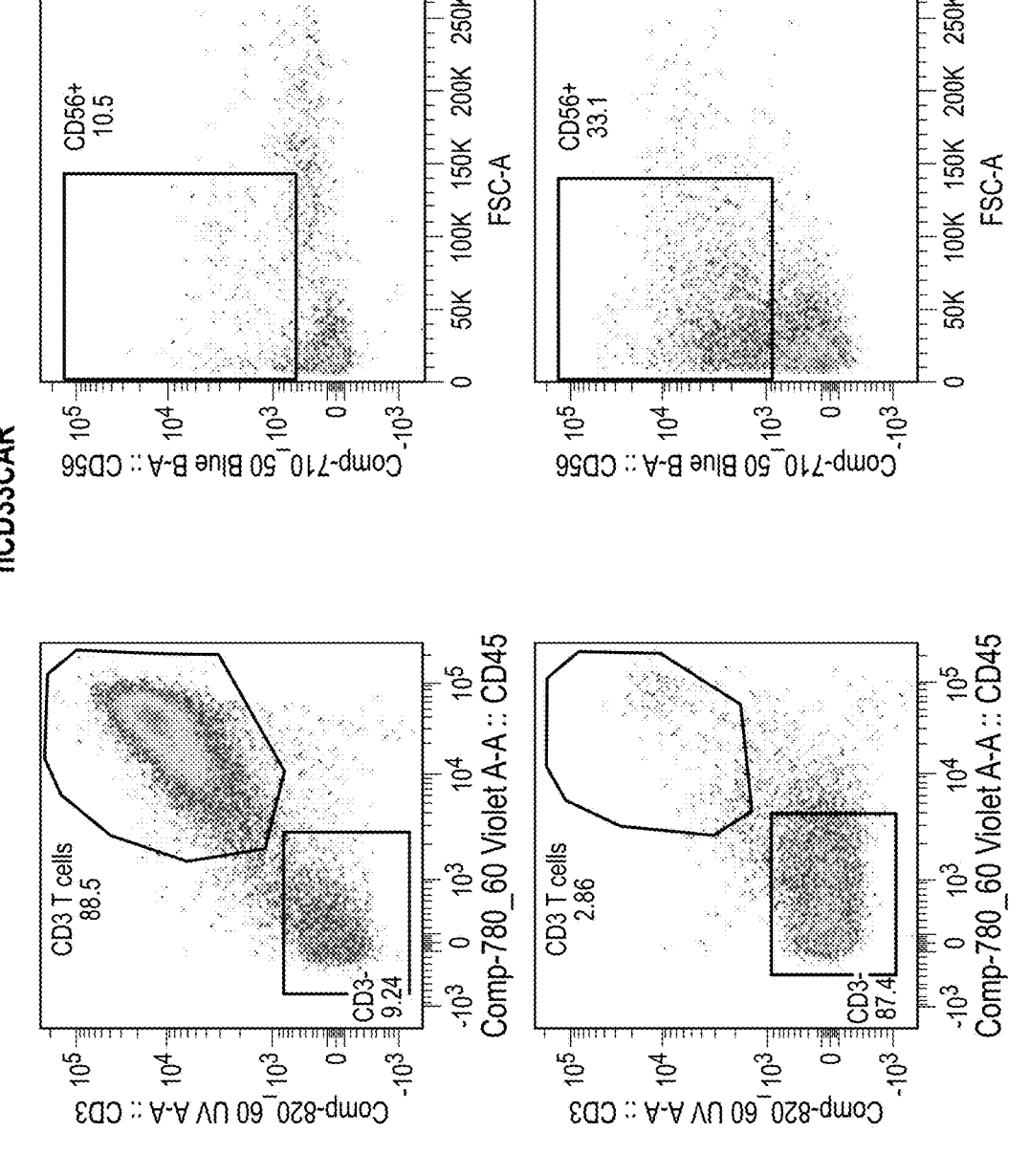
FIGS. 8A, 8B, and 8C show CD56+ expression on CD3− live cells.
Figure 8B:
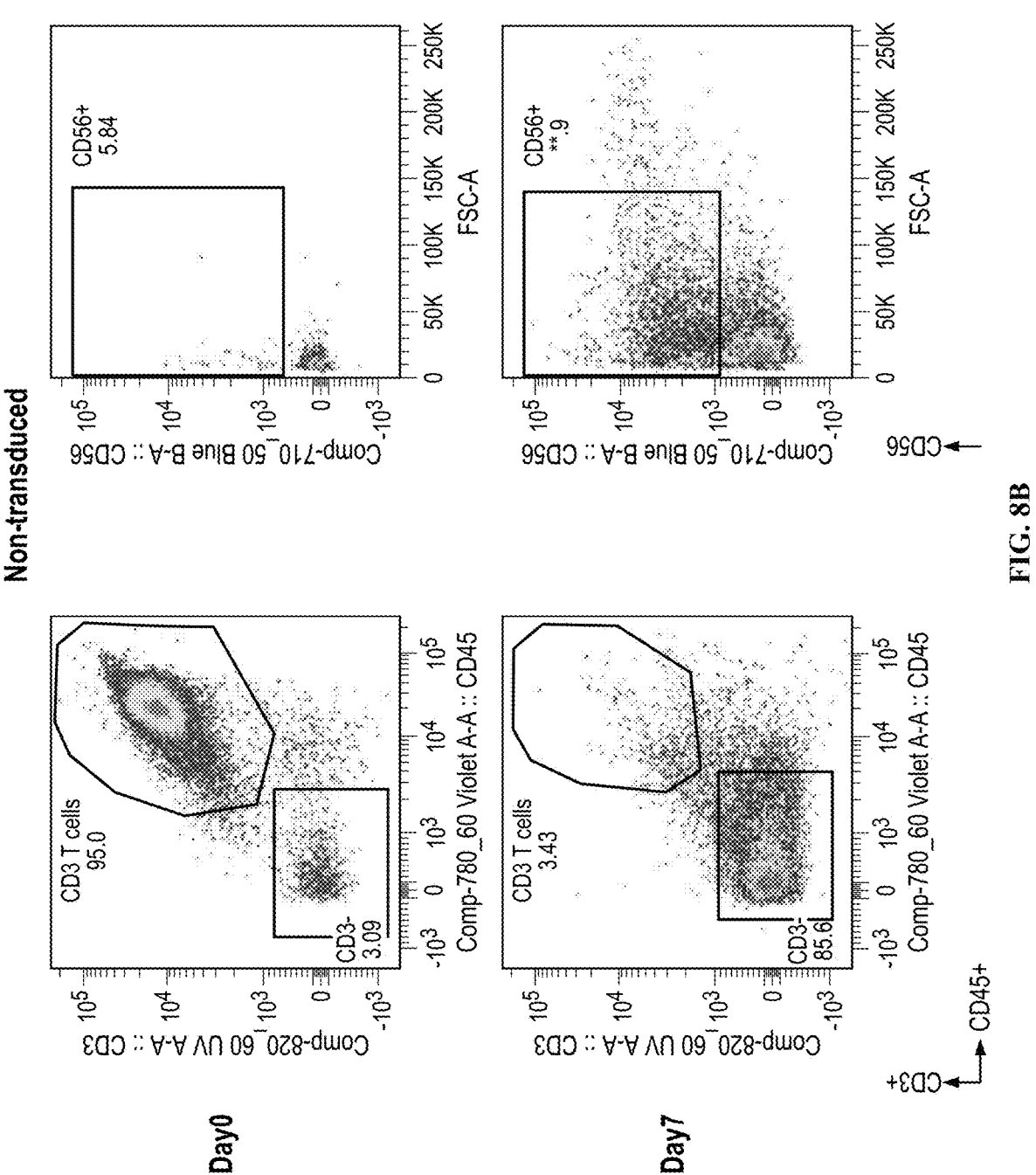
Figure 8C:
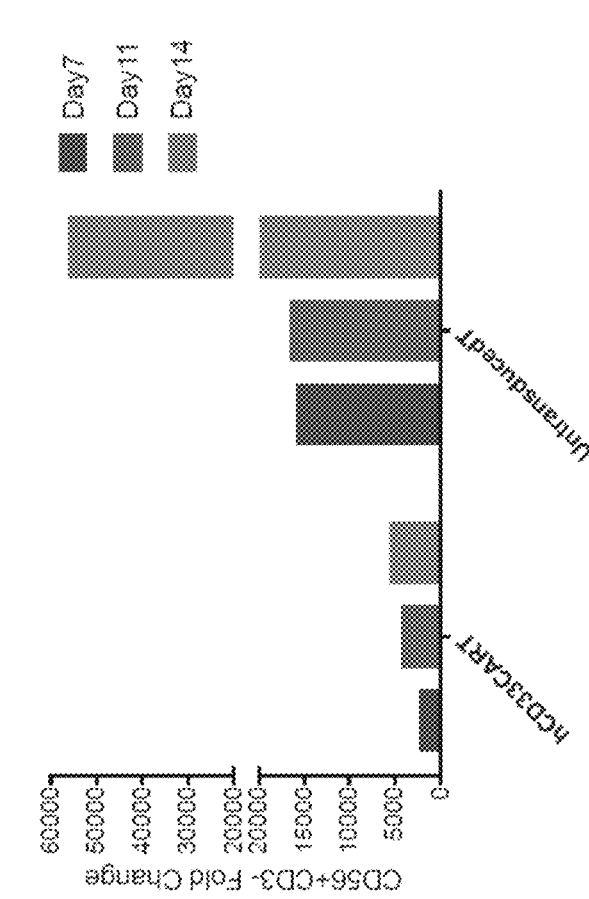

Observing CD56+ expression on CD3− live cells. FIGS. 8A and 8B show that CD56 is expressed on CD3− cells, specifically showing big increase on CD3− cells of non-transduced group. FIG. 8C shows the fold change from non-transduced cells had more than 50,000 increase.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for expanding a γδ T cell from a subject for use in immune therapy, comprising:
   (a) isolating a γδ T cell from peripheral blood of the subject,
   b) providing an artificial antigen presenting cell (aAPC) comprising a cell membrane, wherein the aAPC expresses Protein L and comprises Protein L on its membrane; wherein the aAPC comprises one or more single chain variable fragment (scFv) antibodies or ligands that bind CD28; and
   (c) contacting the peripheral blood-isolated γδ T cell with an effective amount of the aAPC to expand the γδ T cell in an amount effective for immunotherapy.

2. The method of claim 1, wherein the aAPC further expresses one or more scFv antibodies that bind a T cell inhibitory molecule, or a combination thereof.

3. The method of claim 2, wherein the T cell inhibitory molecule comprises PD1, PDL1, or a combination thereof.

4. The method of claim 2, wherein the T cell inhibitory molecule comprises CTLA4, LAG3, TIM3, BTLA, CD160, 2B4, A2aR, KIR, or any combination thereof.

5. The method of claim 1, wherein the cell membrane further comprises on its membrane one or more scFv or ligands that bind a second co-stimulatory molecule on T-cells, one or more scFv antibodies or ligands that selectively bind CD3, or a combination thereof.

6. The method of claim 5, wherein the co-stimulatory molecule comprises 4-1BB.

7. A γδ T cell produced by the method of claim 1.

8. A method for increasing the purity of γδ T cells, comprising
   (a) isolating a γδ T cell from peripheral blood of a subject:
   (b) providing an artificial antigen presenting cell (aAPC) comprising a cell membrane, wherein the aAPC expresses Protein L and comprises Protein L on its membrane; wherein the aAPC comprises one or more scFv antibodies or ligands that bind CD28; and
   (c) incubating the γδ T cell with the aAPC for at least 8 hours; wherein the aAPC induces the γδ T cellto proliferate.

9. The method of claim 8, wherein the γδ T cell is incubated with the aAPC for at least 9, 10, 11, 12, 13, 14, 15, 16, 17, 18, 19, 20, 21, 22, 23, 24, 26, 28, 30, 32, 34, 36, or 48 hours.

10. The method of claim 8, wherein the aAPC further expresses one or more scFv antibodies that bind a T cell inhibitory molecule, or a combination thereof.

11. The method of claim 10, wherein the T cell inhibitory molecule comprises PD1, PDL1, or a combination thereof.

12. The method of claim 10, wherein the T cell inhibitory molecule comprises CTLA4, LAG3, TIM3, BTLA, CD160, 2B4, A2aR, KIR, or any combination thereof.

13. The method of claim 8, wherein the cell membrane contains on its membrane one or more scFv antibodies or ligands that bind a co-stimulatory molecule on T-cells, one or more scFv antibodies or ligands that selectively bind CD3, or a combination thereof.

14. The method of claim 13, wherein the co-stimulatory molecule comprises 4-1BB.

\* \* \* \* \*